US010285624B2

(12) United States Patent
Taylor et al.

(10) Patent No.: US 10,285,624 B2
(45) Date of Patent: May 14, 2019

(54) SYSTEMS, DEVICES, AND METHODS FOR ESTIMATING BILIRUBIN LEVELS

(71) Applicant: University of Washington through its Center for Commercialization, Seattle, WA (US)

(72) Inventors: James A. Taylor, Seattle, WA (US); Shwetak N. Patel, Seattle, WA (US); James W. Stout, Seattle, WA (US); Lilian De Greef, Seattle, WA (US); Mayank Goel, Seattle, WA (US); Eric C. Larson, Seattle, WA (US)

(73) Assignee: University of Washington, Seattle, WA (US)

( * ) Notice: Subject to any disclaimer, the term of this patent is extended or adjusted under 35 U.S.C. 154(b) by 692 days.

(21) Appl. No.: 14/835,348

(22) Filed: Aug. 25, 2015

(65) Prior Publication Data

US 2015/0359459 A1 Dec. 17, 2015

Related U.S. Application Data

(63) Continuation-in-part of application No. PCT/US2014/024761, filed on Mar. 12, 2014.
(Continued)

(51) Int. Cl.
*A61B 5/00* (2006.01)
*A61B 5/103* (2006.01)

(52) U.S. Cl.
CPC .......... *A61B 5/1034* (2013.01); *A61B 5/0077* (2013.01); *A61B 5/443* (2013.01);
(Continued)

(58) Field of Classification Search
CPC ... A61B 5/0013; A61B 5/0059; A61B 5/1455; A61B 5/14551; A61B 5/14552;
(Continued)

(56) References Cited

U.S. PATENT DOCUMENTS 5,671,735 A 9/1997 MacFarlane et al.
6,045,502 A 4/2000 Eppstein et al.
(Continued)

FOREIGN PATENT DOCUMENTS

JP H10165375 A 6/1998
JP 11-506200 A 6/1999
(Continued)

OTHER PUBLICATIONS

Agu, et al. The smartphone as a medical device: Assessing enablers, benefits and challenges. 2013 IEEE International Conference on Sensing, Communications and Networking (SECON), Ieee (2013), 76-80.
(Continued)

*Primary Examiner* — Eric F Winakur
*Assistant Examiner* — Chu Chuan (J J) Liu
(74) *Attorney, Agent, or Firm* — Dorsey & Whitney LLP

(57) ABSTRACT

Systems, methods, and devices are provided for estimating bilirubin levels. In one aspect, a method for estimating the level of bilirubin in a patient includes receiving image data for at least one image including a region of the patient's skin and a color calibration target. Color-balanced image data for the skin region is generated based on a subset of the image data corresponding to the color calibration target and the skin region. The bilirubin level in the patient is estimated based on the color-balanced image data for the skin region.

26 Claims, 20 Drawing Sheets

Related U.S. Application Data

(60) Provisional application No. 61/777,097, filed on Mar. 12, 2013, provisional application No. 62/041,492, filed on Aug. 25, 2014.

(52) U.S. Cl.
CPC ........... *A61B 5/0013* (2013.01); *A61B 5/6898* (2013.01); *A61B 2503/045* (2013.01); *A61B 2576/02* (2013.01)

(58) Field of Classification Search
CPC . A61B 5/14553; A61B 5/14546; A61B 5/443; A61B 5/1032; A61B 5/1034; A61B 5/6898; A61B 5/1495
See application file for complete search history.

(56) References Cited

U.S. PATENT DOCUMENTS

| | | | |
|---|---|---|---|
| 6,128,516 | A | 10/2000 | MacFarlane et al. |
| 6,178,341 | B1 | 1/2001 | MacFarlane et al. |
| 6,305,804 | B1* | 10/2001 | Rice ............... A61B 5/1455 600/323 |
| 6,615,061 | B1 | 9/2003 | Khalil et al. |
| 8,154,612 | B2 | 4/2012 | Quan et al. |
| 2003/0002722 | A1* | 1/2003 | Jay ................ A61B 5/1455 382/128 |
| 2008/0288227 | A1 | 11/2008 | Higgins et al. |
| 2009/0137908 | A1* | 5/2009 | Patwardhan ......... A61B 5/0059 600/476 |
| 2011/0206254 | A1 | 8/2011 | Patwardhan |
| 2013/0296709 | A1 | 11/2013 | Zuzak et al. |
| 2014/0323832 | A1* | 10/2014 | Thangaraj .......... A61B 5/14546 600/315 |
| 2015/0051498 | A1* | 2/2015 | Darty ................ A61B 5/1455 600/477 |
| 2015/0057551 | A1* | 2/2015 | Chou ................ A61B 5/1032 600/477 |

FOREIGN PATENT DOCUMENTS

| | | | |
|---|---|---|---|
| JP | 2000121439 | A | 4/2000 |
| JP | 2004535219 | A | 11/2004 |
| JP | 2009505107 | A | 2/2009 |
| JP | 2010520551 | A | 6/2010 |
| JP | 2010533537 | A | 10/2010 |
| WO | 9641140 | A1 | 12/1996 |
| WO | 02080764 | A1 | 10/2002 |
| WO | 2007022413 | A2 | 2/2007 |
| WO | 2008108760 | A1 | 9/2008 |
| WO | 2009013687 | A2 | 1/2009 |

OTHER PUBLICATIONS

Akman, et al. Transcutaneous Measurement of Bilirubin by Icterometer During Phototherapy on a Bilibed. Turkish Journal of Medical Sciences 32, Jun. 2000 (2002), 165-168.

Baker, et al. Mobile phone-based detection of neonatal jaundice. (Vanderbilt S. of E. BME 272 NCIIA Project Proposal Neonatal Jaundice. 2012. https://my.vanderbilt.edu/mobilemed/proposal/.

Bental, et al. Bhutani-based nomograms for the prediction of significant hyperbilirubinaemia using transcutaneous measurements of bilirubin. Acta paediatrica (Oslo, Norway : 1992) 98, 12 (2009), 1902-8.

Bhutani, et al. Predischarge Screening for Severe Neonatal Hyperbilirubinemia Identifies Infants Who Need Phototherapy. The Journal of pediatrics 162, 3 (2013), 477-482.e1.

Bhutani. Kernicterus as a 'Never-Event': A newborn safety standard? Indian J. Pediatri. 2005; 72:53-56.

Bland, et al. Statistical Methods for Assessing Agreement Between Two Methods of Clinical Measurement. The Lancet, (1986), 307-310.

Boulanger, et al. Stroke rehabilitation with a sensing surface. Changing Perspectives, Paris, France. CHI, (2013); 1243-1246.

Bourouis, et al. An intelligent mobile based decision support system for retinal disease diagnosis. Decision Support Systems 59, (2014), 341-350.

Breiman. Random Forests. Machine Learning 45, 1 (2001), 5-32.

Brooks, et al. Evidence suggests there was not a 'resurgence' of Kernicterus in the 1990s. Pediatrics. 2011; 127:672-679.

Chang, et al. A Kinect-based system for physical rehabilitation: a pilot study for young adults with motor disabilities. Research in developmental disabilities 32, 6 (2011), 2566-70.

Chen, et al. Listen-to-Nose : A low-cost system to record nasal symptoms in daily life. UbiComp '12, (2012); 590-591.

Consolvo, et al. Flowers or a Robot Army ? Encouraging Awareness & Activity with Personal , Mobile Displays. UbiComp '08, (2008); 54-63.

Dell, et al. Mobile Tools for Point-of-Care Diagnostics in the Developing World Categories and Subject Descriptors. DEV '13, (2013). 10 pages.

Efron, et al. Least Angle Regression. The Annals of Statistics 32, 2 (2004), 407-499.

Engle, et al. Assessment of a transcutaneous device in the evaluation of neonatal hyperbilirubinemia in a primarily Hispanic population. Pediatrics. Jul. 2002;110(1 Pt 1):61-7.

Facion. What's My Heart Rate—Measure Your Heart Rate by Just Looking At Your Screen. http://facion.net/WhatsMyHeartRate/. Retrieved Aug. 20, 2015. 6 pages.

Fitbit® OneTM Wireless Activity tracker. http://www.fitbit.com/one. Retrieved Aug. 20, 2015. 11 pages.

Franko, et al. Validation of a scoliometer smartphone app to assess scoliosis. Journal of pediatric orthopedics 32, 8 (2012), e72-5.

Gupta, et al. Adaptive local linear regression with application to printer color management. Image Processing, IEEE Transactions on, (2008), 936-945.

Hutchins. Student honored for science, policy vision to improve biomedicine and human health. Rice BIOE news. Retrieved Aug. 20, 2015. 2 pages.

International preliminary report on patentability dated Sep. 24, 2015 for PCT/US2014/024761.

International search report and written opinion dated Jul. 21, 2014 for PCT/US2014/024761.

Kito health tracker by Azoi Inc. https://azoi.com/. Retrieved Oct. 23, 2015. 9 pages.

Larson, et al. Accurate and privacy preserving cough sensing using a low-cost microphone. Proceedings of the 13th international conference on Ubiquitous computing—UbiComp '11, ACM Press (2011), 375-384.

Larson, et al. SpiroSmart: Using a Microphone to Measure Lung Function on a Mobile Phone. ACM UbiComp, (2012); 280-289.

Leartveravat. Transcutaneous bilirubin measurement in full term neonate by digital camera. 2009. (in Thai with English abstract) 14 pages.

Lee, et al. Atrial fibrillation detection using a smart phone. Conference proceedings : . . . Annual International Conference of the IEEE Engineering in Medicine and Biology Society. IEEE Engineering in Medicine and Biology Society. Conference 2012, (2012), 1177-80.

Lee, et al. Atrial fibrillation detection using an iPhone 4S. IEEE transactions on biomedical engineering 60, 1 (2013), 203-6.

Maisels, et al. Hyperbilirubinemia in the newborn infant > or =35 weeks' gestation: an update with clarifications. Pediatrics. Oct. 2009;124(4):1193-8. doi: 10.1542/peds.2009-0329. Epub Sep. 28, 2009.

Management of Hyperbilirubinemia in the Newborn Infant 35 or More Weeks of Gestation. Pediatrics 114, 1 (2004), 297-316.

Moyer, et al. Accuracy of clinical judgment in neonatal jaundice. Arch Pediatr Adolesc Med. Apr. 2000;154(4):391-4.

Neonatal Jaundice. NICE Clinical guideline 98. London, May 2010. 41 pages.

Nike+. Fitess tracker. https://secure-nikeplus.nike.com/plus/products/. Retrieved Aug. 20, 2015. 4 pages.

Pamplona, et al. NETRA : Interactive Display for Estimating Refractive Errors and Focal Range. SIGGRAPH, (2011).

(56) References Cited

OTHER PUBLICATIONS

Patel. ClikJaundice: Using mobile technology to detect yellow in newborns. Published Jun. 12, 2013. 4 pages. http://thealternative.in/social-business/clickjaundice-using-the-phone-to-prevent-jaundice-in-newborns/.

Philips Respironics Bilichek System with wall mount power supply. Amazon.com. Retrieved Aug. 20, 2015. 4 pages.

Poh, et al. Heartphones: Sensor Earphones and Mobile Application for Non-obtrusive Health Monitoring. 2009 International Symposium on Wearable Computers, (2009), 153-154.

Poland, et al. Comparison of skin sites for estimating serum total bilirubin in in-patients and out-patients: chest is superior to brow. Journal of perinatology : official journal of the California Perinatal Association 24, 9 (2004), 541-3.

Ramer. An Iterative Procedure for the Polygonal Approximation of Plane Curves. Computer Graphics and Image Processing 1, 3 (1972), 244-256.

Rubaltelli, et al. Transcutaneous bilirubin measurement: a multicenter evaluation of a new device. Pediatrics. Jun. 2001;107(6):1264-71.

Shen, et al. Point-of-care colorimetric detection with a smartphone. Lab on a chip 12, 21 (2012), 4240-3.

Slusher, et al. A global need for affordable neonatal jaundice technologies. Seminars in perinatology 35, 3 (2011), 185-91.

Smartphone Ultrasound, MobiUS SP1 | Mobisante. http://www.mobisante.com/products/product-overview/. Retrieved Aug. 20, 2015. 1 page.

Smola, et al. A tutorial on support vector regression. Statistics and computing 14, 3 (2004), 199-222.

Tisdale, et al. The Significance of the Direct-Reacting of Serum Bilirubin in Hemolytic Jaundice. The American Journal of Medicine 26, 2 (1959), 214-227.

Viggiano. Comparison of the accuracy of different white balancing options as quantified by their color constancy Comparison of the accuracy of different white balancing options as quantified by their color constancy. Sensors and Camera Systems for Scientific, Industrial, and Digital Photography ApplicationsV: Proceedings of the SPIE 5301, (2004); 323-333.

Wadhawan, et al. Implementation of the 7-point checklist for melanoma detection on smart handheld devices. Conference proceedings : . . . Annual International Conference of the IEEE Engineering in Medicine and Biology Society. IEEE Engineering in Medicine and Biology Society. Conference, (2011), 3180-3.

Wang, et al. Wound image analysis system for diabetics. Medical Imaging 2013: Image Processing. Proc. of SPIE. 8669; (2013), 866924.

Zou, et al. Regularization and variable selection via the elastic net. Journal of the Royal Statistical Society: Series B (Statistical Methodology) 67, 2 (2005), 301-320.

Notice of Reasons for Rejection for Japanese Patent Application No. 2016-501634, dated Dec. 6, 2017.

Extended European Search Report for EP Appl. No. 14784645.5 dated Dec. 8, 2016.

Unpublished PCT Application No. PCT/US2018/035708, titled "Bilirubin Estimation Using Sclera Color and Accessories Therefor", filed Jun. 1, 2018.

English translation of Japanese Official Action dated Sep. 12, 2018 for Japanese application No. 2016-501634, pp. all.

Int'l Search Report and Written opinion for PCT Application No. PCT/US2018/035708, dated Aug. 9, 2018.

Leung, et al., "Screening neonatal jaundice based on the sclera color of the eye us ing digital photography", Optical Society of America, Nov 2015, vol. 6, No. 11, pp. all.

Mariakakis, et al., "BiliScreen: Smartphone-Based Scleral Jaundice Monitoring for Liver and Pancreatic Disorders", Proc. ACM Interact. Mob. Wearable Ubiquitous Technol. 1, 2, Article 20 (May 2017), 26 pages.

\* cited by examiner

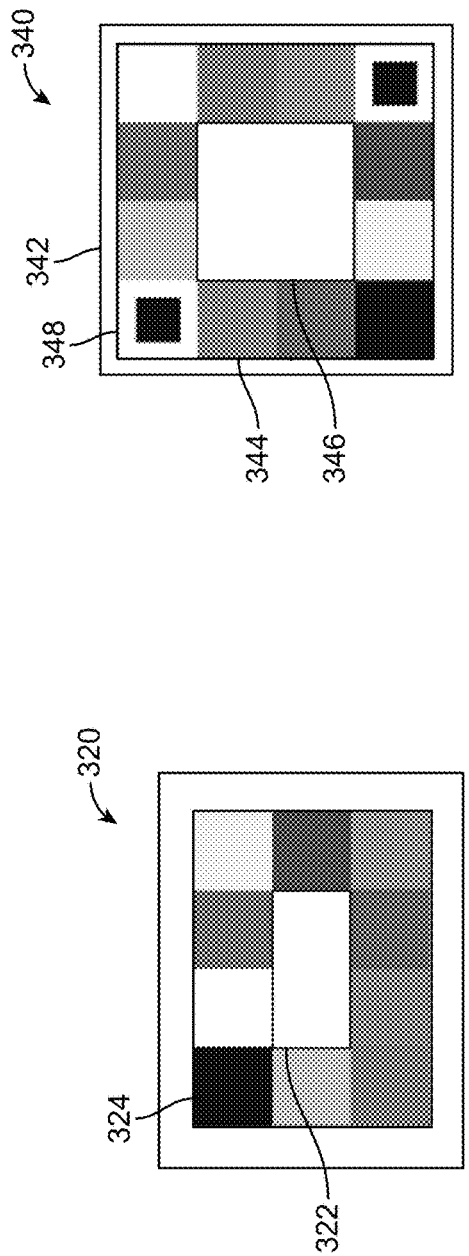
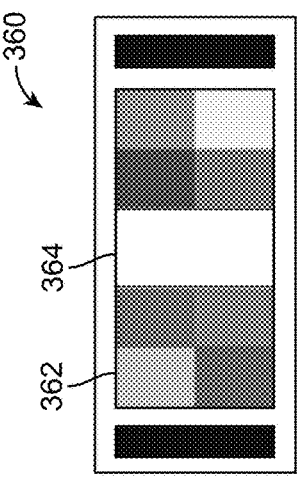
FIG. 3C
FIG. 3D
FIG. 3B

SYSTEMS, DEVICES, AND METHODS FOR ESTIMATING BILIRUBIN LEVELS

CROSS-REFERENCE

This application is a continuation-in-part application and claims the benefits of U.S. Provisional Application No. 62/041,492, filed Aug. 25, 2014 and PCT Application No. PCT/US2014/024761, filed Mar. 12, 2014, which claims the benefit of U.S. Provisional Application No. 61/777,097, filed Mar. 12, 2013; the entire disclosures of which are incorporated herein by reference.

BACKGROUND

An estimated 60-84% of newborn infants develop neonatal jaundice, which produces a yellowing of the skin caused by the accumulation of excess bilirubin (hyperbilirubinemia), a naturally occurring compound produced by the breakdown of red blood cells. Although this condition is typically harmless and resolves within a few days, highly elevated levels of bilirubin can lead to kernicterus, a devastating and irreversible neurological condition characterized by deafness, cerebral palsy, profound developmental delay, or even death.

Current approaches for monitoring bilirubin levels in infants typically require repeated testing in a hospital setting. The blood concentration of bilirubin can be determined by the total serum bilirubin (TSB) measured from a blood sample, or via a transcutaneous bilirubinometer (TcB) measurement accomplished using a non-invasive but costly instrument. These tests are often unavailable in resource-poor settings, thus impeding early detection and treatment of kernicterus. Visual assessments, which are frequently used as an alternative to these tests, are often inaccurate and can be confounded by factors such as lighting or skin tone. Accordingly, improved approaches are needed for providing non-invasive, cost-effective screening for excessive bilirubin levels.

SUMMARY

Systems, methods, and devices are provided for estimating bilirubin levels. In many embodiments, a mobile device is used to capture image data of a patient's skin and a color calibration target. The image data is processed to generate an estimation of the bilirubin level. The image processing can include transforming the image data into a plurality of different color spaces to facilitate assessment of the overall yellowness of the skin while compensating for color differences caused by lighting, skin tone, and other potentially confounding factors. The screening techniques described herein can be practiced by users (e.g., parents, medical professionals, community health workers) in an outpatient setting (e.g., a patient's home) without requiring specialized medical equipment, thereby improving the convenience, accessibility, and cost-effectiveness of bilirubin monitoring.

Thus, in a first aspect, a method is provided for estimating the level of bilirubin in a patient. The method includes receiving image data for at least one image including a region of the patient's skin and a color calibration target. Color-balanced image data for the skin region is generated based on a subset of the image data corresponding to the color calibration target and the skin region. The bilirubin level in the patient is estimated based on the color-balanced image data for the skin region. In many embodiments, the image data can be obtained with any suitable imaging device. The imaging device can collect image data independently of additional attachments or equipment, such as external lenses, filters, or other specialized hardware.

The bilirubin level can be estimated using only image data of the patient's skin color at a particular point in time, or by comparing the skin color image data to baseline skin color image data. For example, the method can further include receiving baseline skin color data for the patient corresponding to when the patient has a reference bilirubin level (e.g., approximately zero when baseline data is obtained within 24 hours of birth). The bilirubin level can be estimated based on one or more differences between the baseline skin color data and the color-balanced image data for the skin region. The baseline skin color data for the patient can be generated by capturing baseline image data for the patient when the patient has the reference bilirubin level. The baseline image data can correspond to at least one image including the skin region and a baseline color calibration target. Color-balanced baseline image data for the skin region can be generated based on a subset of the baseline image data corresponding to the baseline color calibration target and the skin region. The baseline skin color data can be generated based on the color-balanced baseline image data for the skin region.

A standardized color calibration target can be used to facilitate the color balancing process. The color calibration target can include a plurality of standardized color regions, including a white color region. The standardized color regions can include a black region, a gray region, a light brown region, a cyan region, a magenta region, a yellow region, and a dark brown region. The color calibration target can at least partially define an opening configured to expose the skin region to permit capturing of image data for the skin region. The standardized color regions can be disposed in a known arrangement surrounding the opening. Accordingly, the process for generating color-balanced image data for the skin region can include processing the received image data to identify a subset of the image data corresponding to the exposed skin region and a subset of the image data corresponding to the white color region. The white color region data can be processed to determine observed color values for the white color region. Color-balanced image data for the exposed skin region can be generated based on the observed color values for the white color region. The observed color values for the white color region can include any suitable color space values, such as red, green, blue (RGB) color space values.

The image data can be transformed into a plurality of different color spaces in order to detect yellow discoloration of the skin. For example, the color-balanced image data for the skin region can include RGB color space data, and a method of estimating the level of bilirubin in a patient can further include transforming the RGB color space data into at least one other color space to generate color-balanced image data for the exposed skin region for the at least one other color space. The at least one color space can include: (a) a cyan, magenta, yellow, and black (CMYK) color space; (b) a YCbCr color space; and/or (c) a Lab color space.

A plurality of chromatic and achromatic features can be generated based on the image data. In some instances, the received image data can include an image obtained using flash illumination and an image obtained without using flash illumination. Estimating the bilirubin level can include processing a plurality of normalized chromatic and achromatic features to select a first estimated range of the bilirubin level from one of a plurality of different bilirubin ranges. The features can be processed using an approach based on the selected first estimated range of the bilirubin level to generate a final estimate of the bilirubin level. The plurality of different bilirubin ranges can include a low range, a medium range, and a high range. The plurality of features can include selected color values of the skin region for a plurality of different color spaces. In some instances, the plurality of features can include a calculation of a color gradient across the skin region.

Estimation of the bilirubin level can involve performing one or more regressions. For example, processing the features to select a first estimated range of the bilirubin level can include performing a series of regressions, including at least one of: (a) a linear regression, (b) an encapsulated k-Nearest Neighbor regression, (c) a lasso regression, (d) a LARS regression, (e) an elastic net regression, (f) a support vector regression using a linear kernel, (g) a support vector regression assigning higher weight to higher-rated bilirubin values, and/or (h) a random forest regression. Processing the features to select a first estimated range of the bilirubin levels can include performing a series of regressions, including: (a) a linear regression, (b) an encapsulated k-Nearest Neighbor regression, (c) a lasso regression, (d) a LARS regression, (e) an elastic net regression, (f) a support vector regression using a linear kernel, (g) a support vector regression assigning higher weight to higher-rated bilirubin values, and (h) a random forest regression. Using a processing approach based on the selected first estimated range of the bilirubin level can include performing a final random forest regression that uses the plurality of normalized chromatic and achromatic features and the selected first estimated range of the bilirubin level as the features for the final random forest regression. In some instances, estimating the bilirubin level includes determining color space value for the patient's skin and using a processing approach based on the determined color space value to estimate the bilirubin level. The regression equations can also include features from the baseline image (e.g., color space values from one or more color spaces).

In another aspect, a mobile device configured to estimate the level of bilirubin in a patient is provided. The device includes a camera operable to capture image data for a field of view, a processor operatively coupled with the camera, and a data storage device operatively coupled with the processor. The data storage device can store instructions that, when executed by the processor, cause the processor to receive image data for an image captured by the camera, the image including a region of the patient's skin and a color calibration target. The instructions can cause the processor to generate color-balanced image data for the skin region based on a subset of the image data corresponding to the color calibration target and the skin region, and estimate the bilirubin level in the patient based on the color-balanced image data for the skin region. In many embodiments, the mobile device can be used to estimate the bilirubin level independently of any external attachments to the mobile device (e.g., lenses, filters) or any other specialized mobile device equipment.

The color calibration target can at least partially define an opening configured to expose the skin region to permit capturing of image data for the skin region, and can include a plurality of standardized color regions including a white color region. The instructions can cause the processor to process the received image data to identify a subset of the image data corresponding to the exposed skin region and a subset of the image data corresponding to the white color region. The white color region data can be processed to determine observed color values for the white color region. Color-balanced RGB image data can be generated for the exposed skin region based on the observed color values for the white color region. Color-balanced image data for the exposed skin region can be generated for at least one other color space by transforming the color-balanced RGB image data into the at least one other color space. A plurality of normalized chromatic and achromatic features can be processed to select a first estimated range of the bilirubin level from one of a plurality of different bilirubin ranges. The features can be processed using an approach based on the selected first estimated range of the bilirubin level to generate a final estimate of the bilirubin level.

Alternatively or in addition, the color-balanced image data for the exposed skin region can be processed to determine a color space value for the patient's skin. A plurality of normalized chromatic and achromatic features can be processed using an approach based on the determined patient's skin color space value to estimate the bilirubin level.

The mobile devices described herein can further include a flash unit operable to selectively illuminate the field of view. The received image data processed to estimate the bilirubin level can include an image captured with the field of view being illuminated by the flash unit and an image captured with the field of view not being illuminated by the flash unit.

In another aspect, a method for estimating the level of bilirubin in a patient is provided. The method includes receiving, from a mobile device, image data for an image including a skin region of a patient and a color calibration target. Color-balanced image data for the skin region can be generated based on a subset of the image data corresponding to the color calibration target and the skin region, via one or more processors. The bilirubin level in the patient can be estimated based on the color-balanced image data for the skin region, via the one or more processors. The estimated bilirubin level can be transmitted to the mobile device. In many embodiments, at least one of receiving the image data and transmitting the estimated bilirubin level are performed using short message service (SMS) text messaging. The image data can be obtained by the mobile device without the use of external attachments, hardware add-ons, or any other specialized equipment.

Other objects and features of the present invention will become apparent by a review of the specification, claims, and appended figures.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A through FIG. 3D illustrate color calibration targets used in conjunction with a mobile device to capture image data used to estimate bilirubin level, in accordance with many embodiments;

DETAILED DESCRIPTION

The systems, devices, and methods described herein provide improved approaches for estimating the bilirubin level in a patient (e.g., an infant or an adult). In many embodiments, the bilirubin level is estimated based on the visual characteristics of the patient's skin as determined from image data (e.g., pictures, videos). Color balancing can be applied to compensate for variations in the image data due to different lighting conditions. For example, the systems, methods, and devices described herein can be used to color balance images of the patient's skin, extract intensities of various reflected wavelengths and other chromatic and/or achromatic properties from the skin, and estimate bilirubin levels (e.g., using machine learning or other suitable algorithms).

In many embodiments, a mobile device configured with suitable software can be used to capture images of a patient's skin and a standardized color calibration target. The image data of the skin and target can be used to generate color-balanced image data that is analyzed to estimate the bilirubin level in the patient. For example, the color-balanced image data can be transformed into a plurality of different color spaces in order to extract features representative of the yellowness of the skin, and these features can be used in a plurality of regressions to generate the bilirubin estimate.

Contrary to existing approaches for measuring bilirubin level, which either rely upon an invasive blood test or utilize costly instrumentation, the systems, devices, and methods described herein enable convenient, portable, and inexpensive bilirubin level estimation that can easily be performed by non-medical personnel using a personal mobile device, thereby improving the accessibility and cost-effectiveness of bilirubin monitoring. Advantageously, the methods described herein can be performed on a mobile device without requiring the use of external attachments, hardware add-ons, or any other specialized mobile device equipment. Notably, the disclosed techniques provide accurate bilirubin level estimation over a large range of bilirubin concentrations, in contrast to TcB measurement which exhibits reduced accuracy at high bilirubin levels. Additionally, the methods described herein account for diversity in skin tones as well as different lighting conditions, thereby improving the accuracy and flexibility of non-invasive bilirubin level estimation. Furthermore, the use of mobile device software platforms enables easy and rapid updating of the estimation methods and algorithms described herein, thus allowing improvements and upgrades to be made as necessary.

Figure 1A:
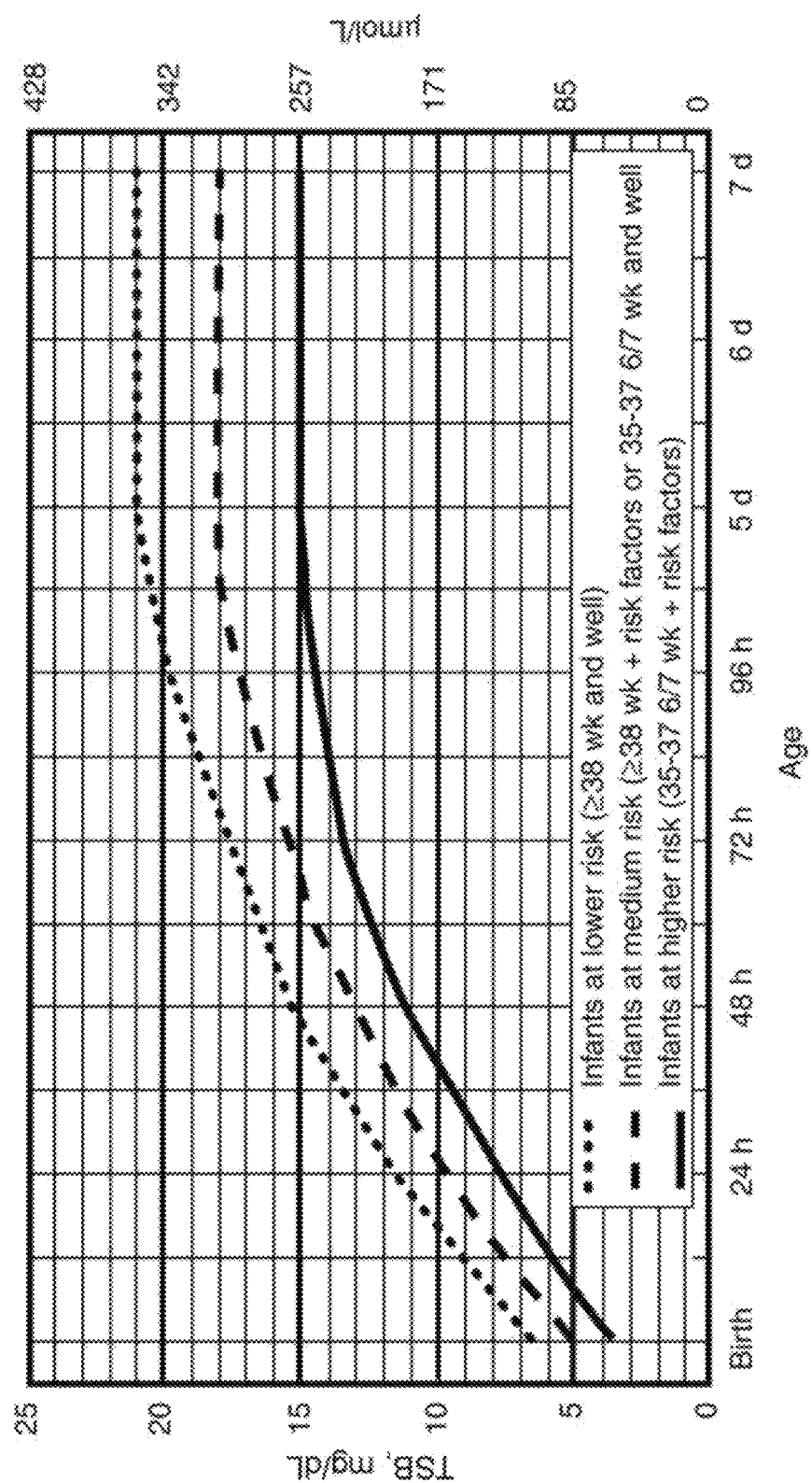
FIG. 1A illustrates guidelines for the use of phototherapy to treat neonatal jaundice, in accordance with many embodiments.
Figure 1B:
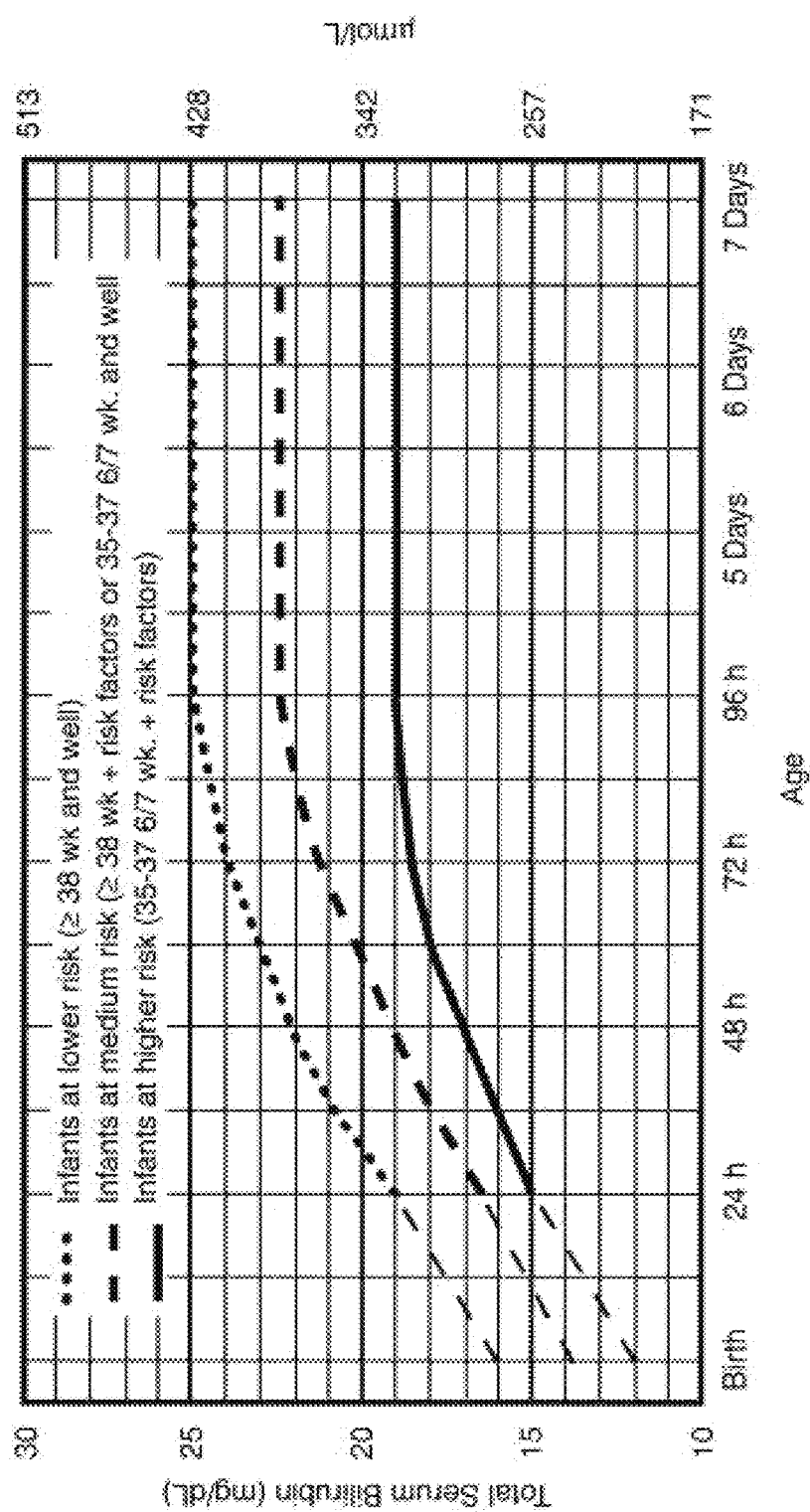
FIG. 1B illustrates guidelines for the use of exchange transfusion to treat neonatal jaundice, in accordance with many embodiments.

Turning now to the drawings, FIG. 1A illustrates guidelines for the use of phototherapy to treat neonatal jaundice. Similarly, FIG. 1B illustrates guidelines for the use of exchange transfusion to treat neonatal jaundice. The guidelines can be used by a medical professional to determine the appropriate course of treatment, based on the infant's age, total serum bilirubin (TSB), number of weeks of gestation (e.g., ≥35 weeks), and other risk factors. Risk factors may include isoimmune hemolytic disease, G6PD deficiency, asphyxia, significant lethargy, temperature instability, sepsis, acidosis, or an albumin level lower than 3.0 grams per deciliter. The curves depicted in FIGS. 1A and 1B indicate exemplary treatment thresholds for low risk, medium risk, and high risk infants.

Figure 1C:
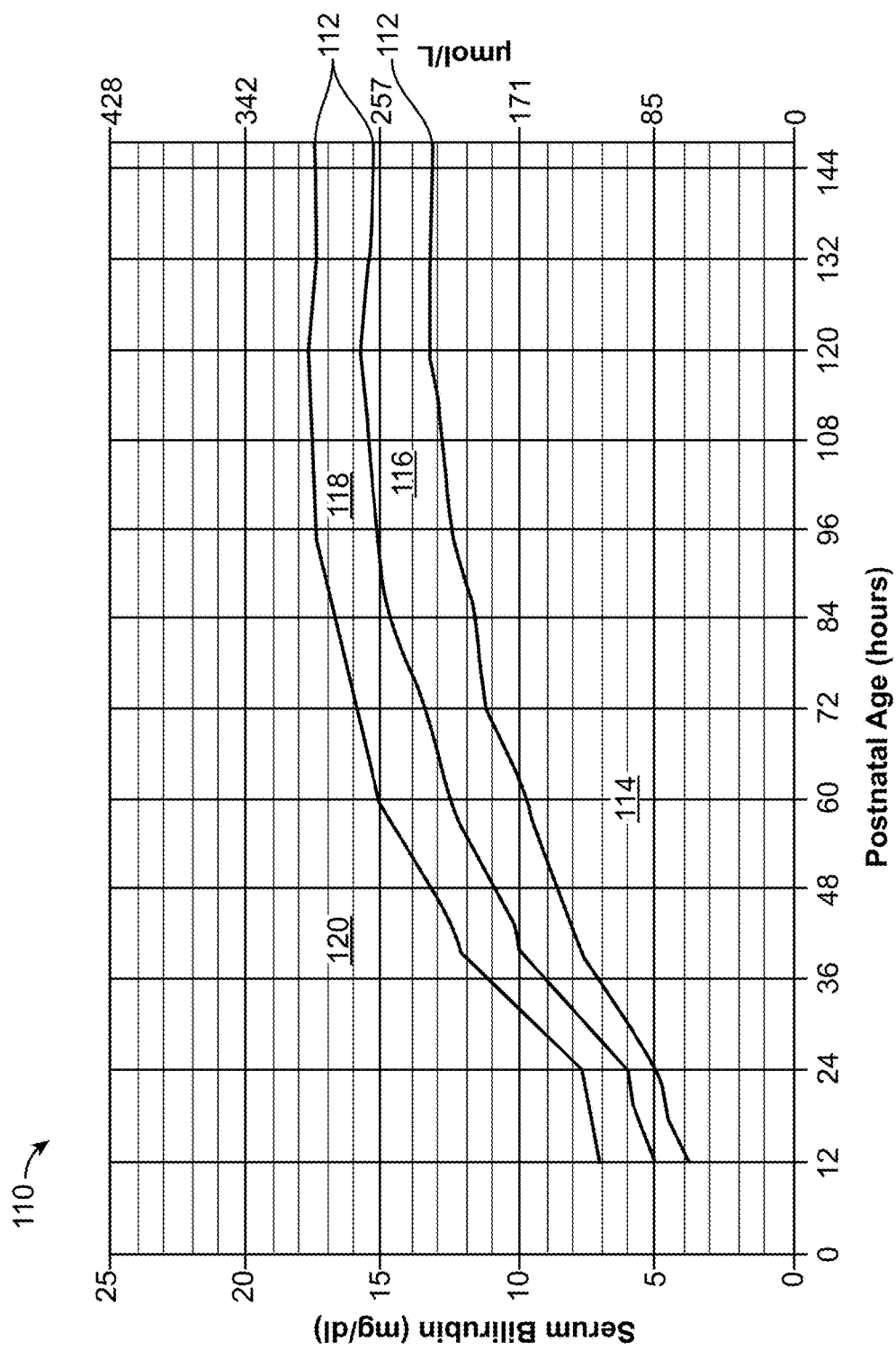
FIG. 1C illustrates a Bhutani nomogram for assessing risk associated with neonatal jaundice, in accordance with many embodiments.

FIG. 1C illustrates a Bhutani nomogram 110 for assessing risk associated with neonatal jaundice. The Bhutani nomogram 110 can be used by a medical professional to assess an infant's risk for developing hyperbilirubinemia based in the infant's postnatal age and bilirubin level. For example, the Bhutani nomogram 110 can include a plurality of percentile curves 112 used to define a low risk zone 114, a low intermediate risk zone 116, a high intermediate risk zone 118, and a high risk zone 120.

Figure 2:
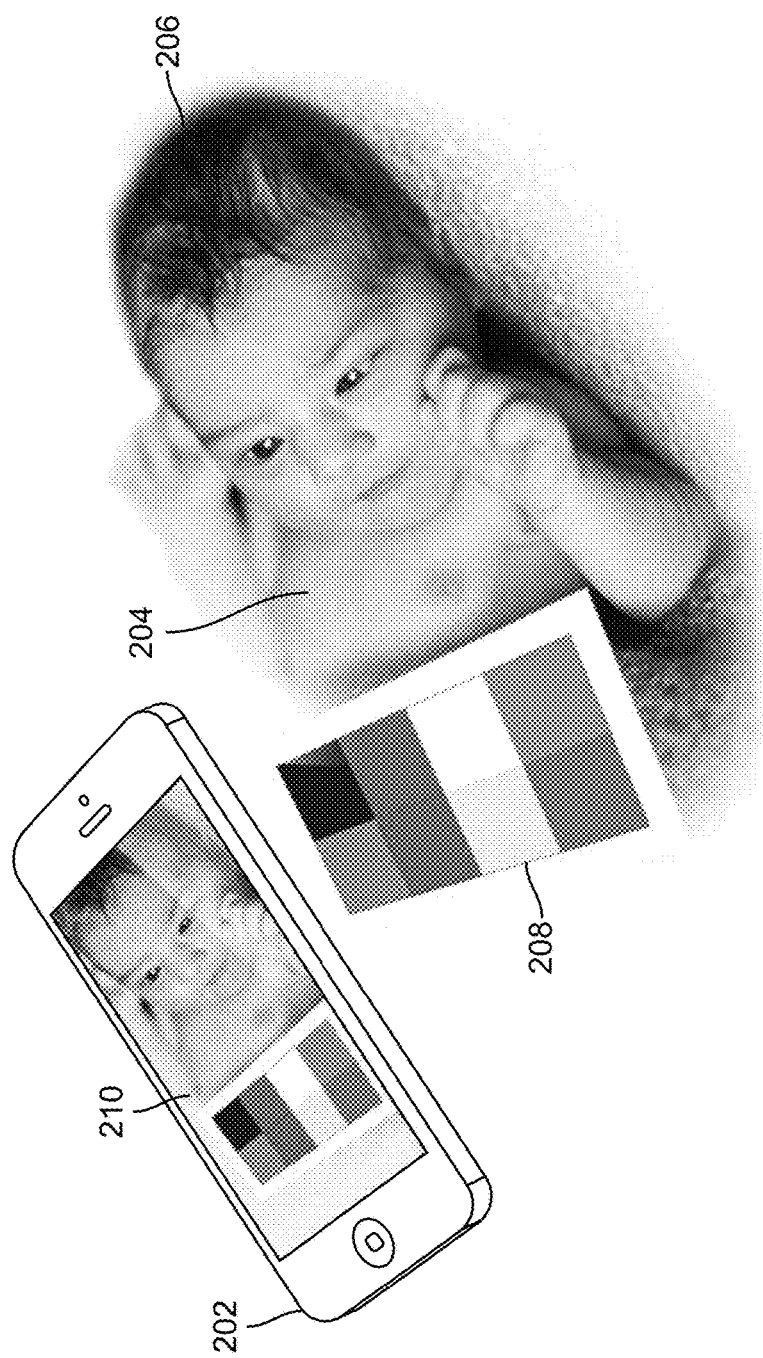
FIG. 2 illustrates the use of a mobile device to capture image data used to estimate the bilirubin level in a patient, in accordance with many embodiments.

FIG. 2 illustrates mobile device-based estimation of bilirubin levels, in accordance with many embodiments. An imaging device, such as a mobile device 202 (e.g., a smartphone, tablet) is used to capture an image of a skin region 204 of a patient 206 and a color calibration target 208. Suitable skin regions for the approaches described herein include the forehead and sternum, as well as any other prominent, flat regions of skin that are likely to be evenly lit. Additionally, since jaundice typically first appears on the forehead and slowly progresses downward on the body, regions closer to the forehead can potentially be more informative for diagnosis. Accordingly, in many embodiments, the color calibration target 208 is placed on the abdomen of the patient 206 near the sternum. The mobile device 202 includes a camera (not shown) for recording image data, as well as a display 210 used for presenting a user interface (UI) of a mobile software application ("mobile app" or "app") for estimating bilirubin levels based on the image data. The mobile device 202 can be a personal device of a user (e.g., a parent, medical professional, community health worker, etc.), such that the user need only install the mobile app on their personal device in order to perform the methods described herein, with no other instrumentation or hardware being needed besides the color calibration target 208. Notably, the mobile device 202 can be used to practice the methods described herein independently of any further attachment or accessory to the mobile device, such as an external lens, filter, or other specialized mobile device equipment. Additional details on suitable software and hardware components for the mobile device 202 are provided in further detail below.

Figure 3A:
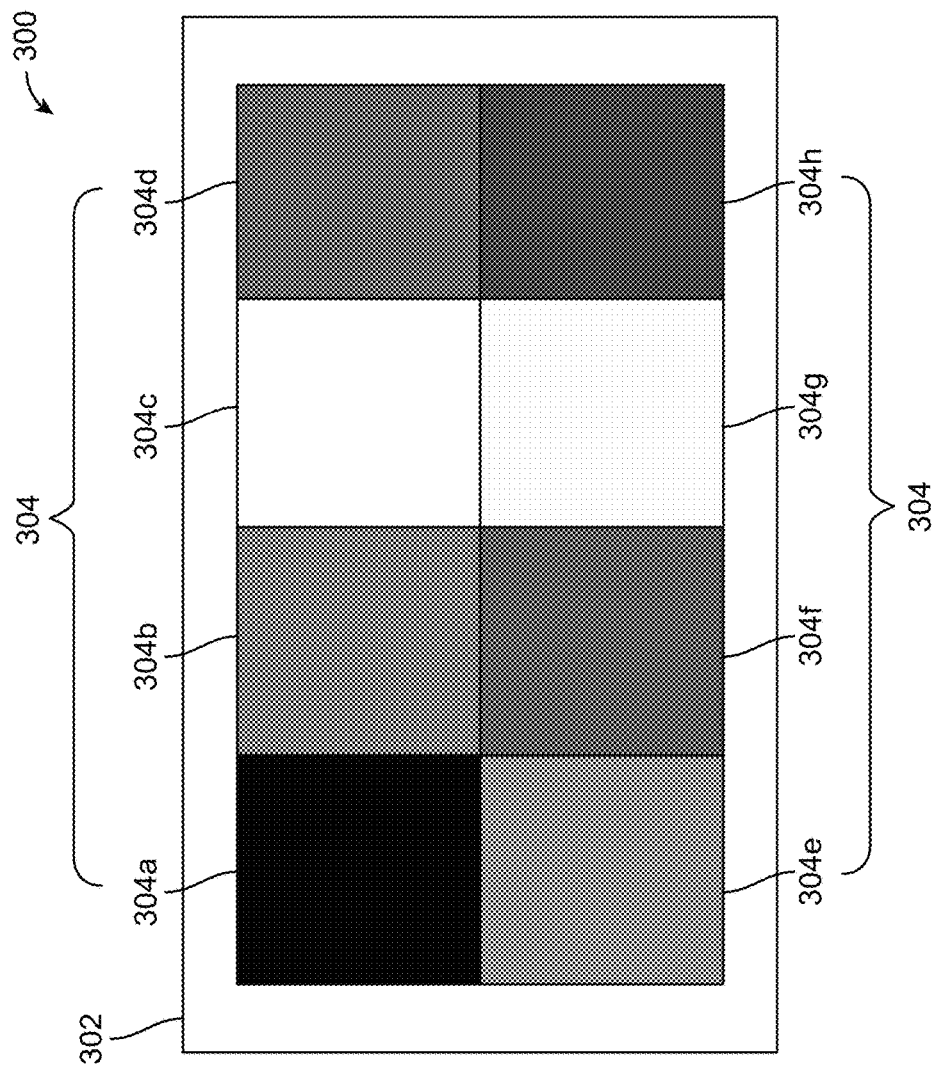

FIG. 3A through FIG. 3D illustrate color calibration targets that can be used in conjunction with a mobile device for estimating bilirubin levels, in accordance with many embodiments. The color calibration targets described herein (also known as "color calibration cards" and "color cards") can be used to account for differences in lighting or other environmental conditions that affect the resultant color balance of the skin image data. Referring to FIG. 3A, a color calibration target 300 can be provided on a rectangular card 302. The card 302 can be cardstock of any size suitable for placement onto the skin of a patient (e.g., an infant), such as approximately the size of a business card. In some instances, the card 302 can be sterilizable or disposable, so as to prevent the spread of pathogens between patients. The color calibration target 300 can include a plurality of standardized colored regions 304, which can be printed onto the card 302. The colored regions 304 can be of any suitable size, number, or shape (e.g., square, rectangular, polygonal, circular, elliptical, etc.). For example, the color calibration target 300 is depicted as including eight identically-sized square colored regions 304*a*-*h*. Each of the standardized colored regions 304 can be of a different color (e.g., black, gray, white, cyan, magenta, yellow, light brown, dark brown) and be positioned in a known arrangement on the card 302. For example, in the embodiment of FIG. 3A, 304*a* is a black region, 304*b* is a gray region (e.g., 50% gray), 304*c* is a white region, 304*d* is a light brown region (e.g., a first skin tone), 304*e* is a cyan region, 304*f* is a magenta region, 304*g* is a yellow region, and 304*h* is a dark brown region (e.g., a second skin tone). Other arrangements and combinations of colors can also be used. Furthermore, the back side (not shown) of the card 302 can include one or more adhesive regions enabling the card 302 to be removably attached to the patient's skin. The back side can also include relevant instructions, such as instructions for the user on how to download the accompanying mobile app onto their personal mobile device.

FIG. 3B illustrates an alternative embodiment of a color calibration target 320. The color calibration target 320 is substantially similar to the color calibration target 300, except it also defines an opening 322. The opening 322 can constrain the calibration target 300 to lie flush with the skin of the patient for more consistent lighting. The opening 322 can be positioned such that when the color calibration target 300 is placed on the patient, the skin region of interest is exposed through the opening 322. The opening 322 can be entirely defined (e.g., completely surrounded) or partially defined (e.g., partially surrounded) by the target 320. A plurality of standardized color regions 324, including a white color region, can be positioned around the opening 322 in a known arrangement. The embodiment of FIG. 3B further includes light gray, medium gray, and dark gray color regions for a total of 10 different standardized color regions. FIG. 3C illustrates a color calibration target 340 provided on a square card 342, with a plurality of standardized color regions 344 surrounding a square opening 346. Some of the color regions 344 can include more than one color, such as color region 348, which includes a central black square bordered by white. FIG. 3D illustrates a color calibration target 360 having a plurality of standardized color regions 362 surrounding an opening 364. The opening 364 can be adjacent to some or all of color regions 362. The color regions 362 are depicted in FIG. 3D as a series of rectangular regions with differing aspect ratios. The colors, geometry, and arrangement of the color regions of the color calibration targets described herein can be selected based on the image processing and analysis methods to be used, such as the embodiments discussed below.

Figure 4A:
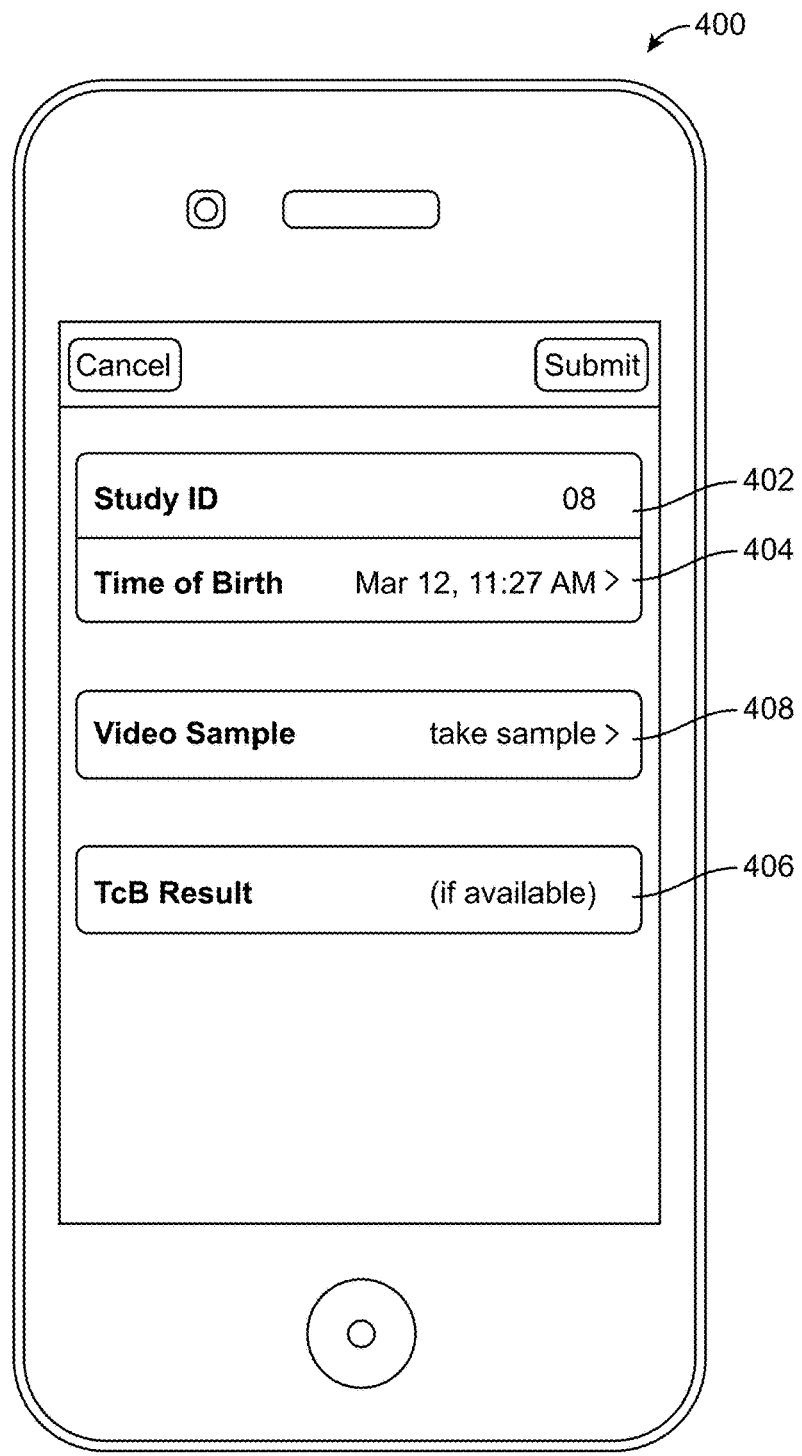
FIG. 4A through FIG. 4C illustrate exemplary user interfaces of a mobile application for estimating bilirubin level, in accordance with many embodiments.
Figure 4B:
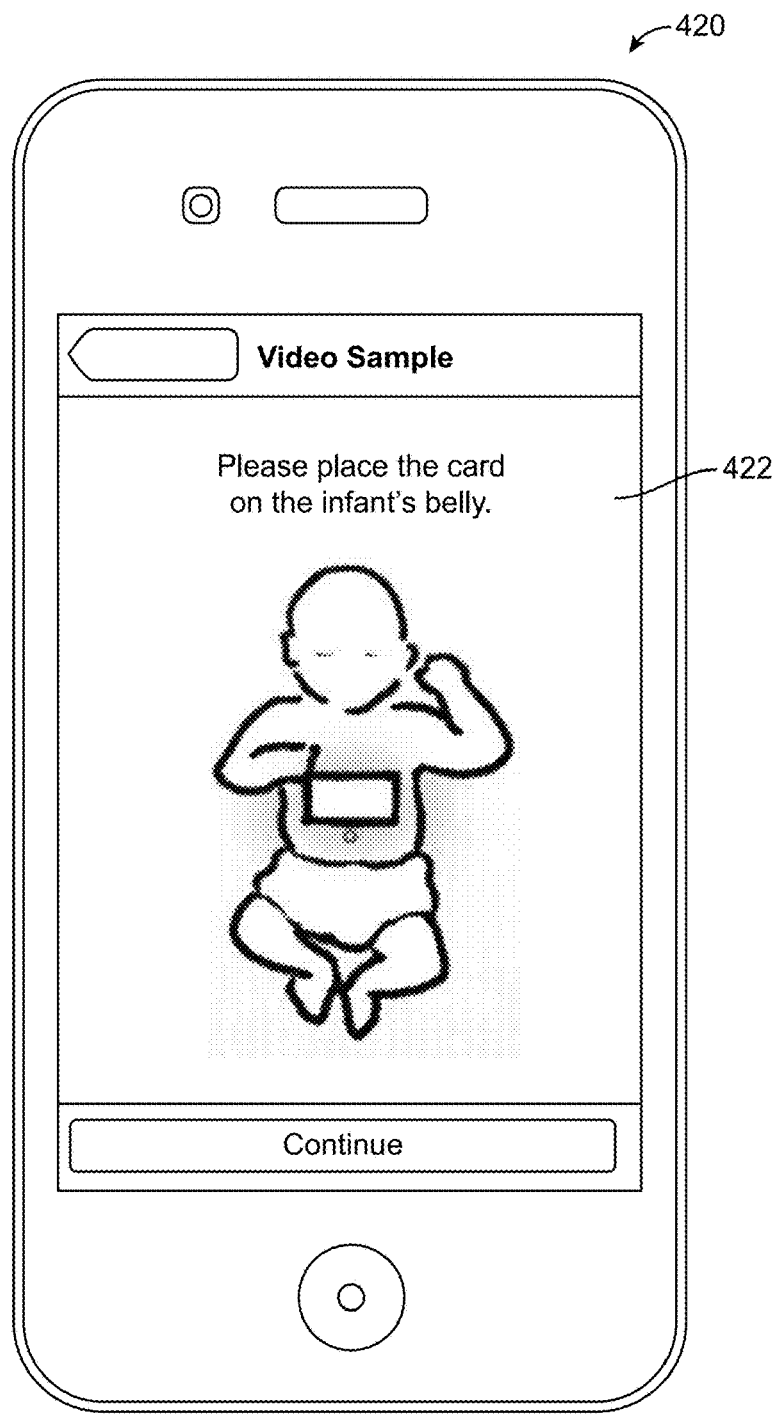
Figure 4C:
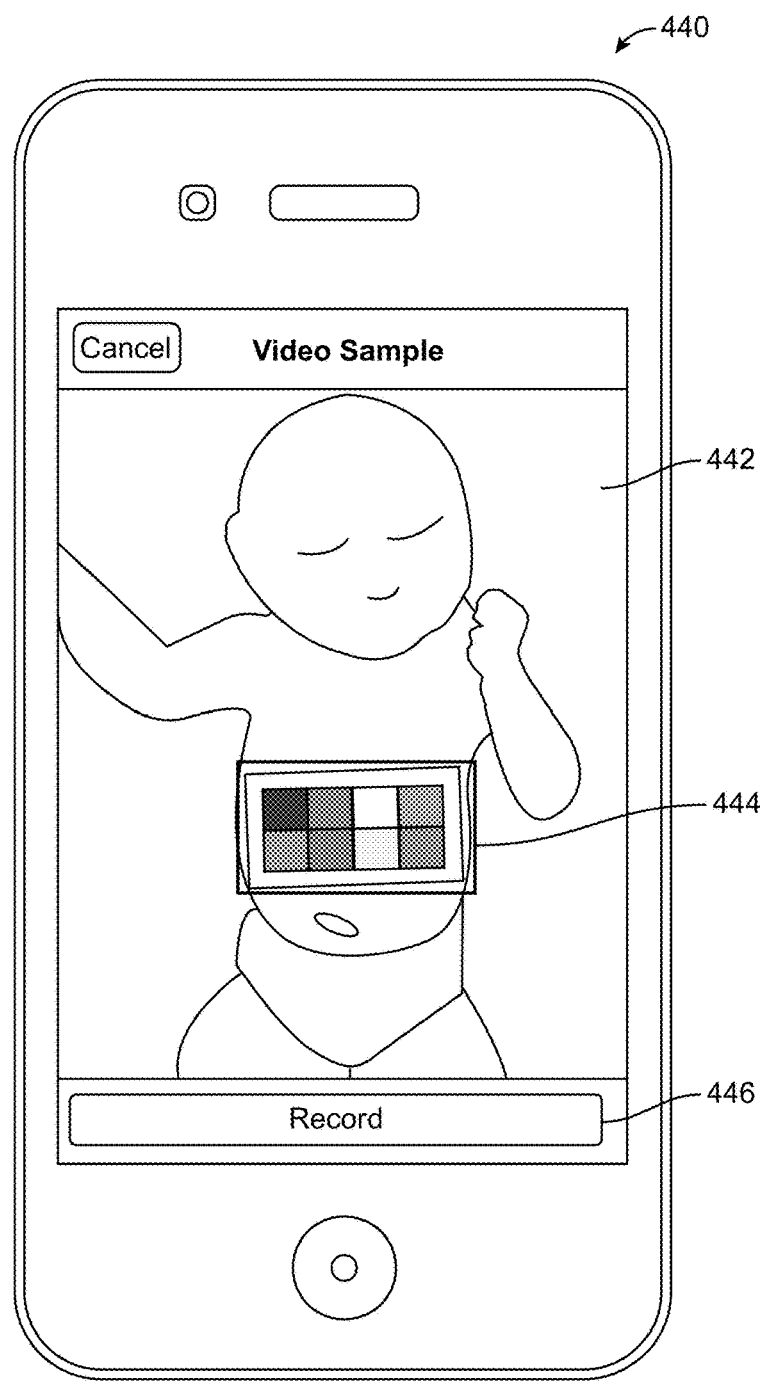

FIG. 4A through FIG. 4C illustrate exemplary user interfaces (UIs) of a mobile app for estimating bilirubin level, in accordance with many embodiments. FIG. 4A illustrates a summary UI 400 for displaying various statistics and metrics relating to a patient. The UI 400 can include patient identification information 402 (e.g., a patient name, study ID number), time of birth 404, and any available bilirubin level results 406 (e.g., TSB and/or TcB results). The UI 400 can also include a button 408 or other interactive elements enabling the user to collect image data (e.g., a video sample or photographic sample) of a patient. In some instances, video samples can be advantageous for eliminating issues of motion blur. FIG. 4B illustrates an instruction UI 420 for assisting a user with capturing image data of a patient. The UI 420 can include graphical and/or textual instructions 422 directing the user to perform the appropriate steps. For example, the instructions 422 can instruct the user to place a color calibration target onto the abdomen of the patient below the sternum. In many embodiments, the instructions 422 are adapted to be easily comprehended by individuals without medical training, thereby allowing non-medical professionals to operate the mobile app. FIG. 4C illustrates a live preview UI 440 displayed to a user during the image capture process. The UI 440 can include a video preview 442 of the current field of view of the camera of the mobile device. The UI 440 can include one or more positioning targets 444 to assist the user in positioning the mobile device. For example, the positioning target 444 can be a box, frame, or colored region overlaid onto the video preview 422 to indicate the appropriate placement of the color calibration target. The size and location of the positioning target 444 can be selected to constrain the distance of the mobile device from the patient to within an optimal range, and also to ensure that the field of view adequately captures the appropriate skin regions and the color calibration target. Once the field of view is correctly aligned, the user can record image data by tapping a record button 446. Additional details regarding the image collection and analysis process are provided below.

Figure 5A:
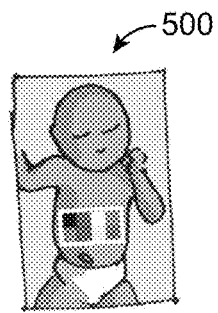
FIG. 5A through FIG. 5F illustrate exemplary image data collected for use in estimating bilirubin level, in accordance with many embodiments.
Figure 5B:
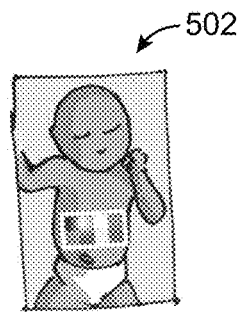
Figure 5C:
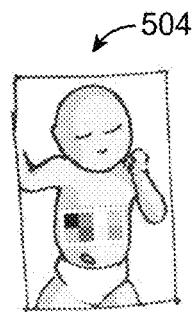
Figure 5D:
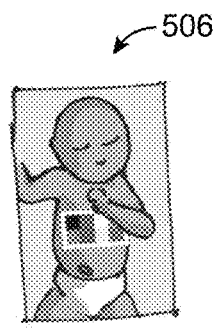
Figure 5E:
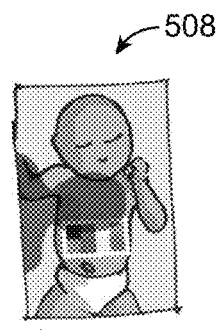
Figure 5F:
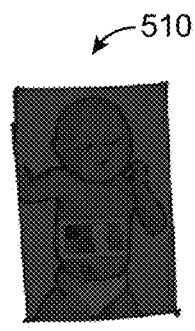

FIG. 5A through FIG. 5F illustrate exemplary image data collected by the mobile app, in accordance with many embodiments. Following the recording process, the mobile app can display the image data to the user for review and approval. Furthermore, in order to ensure that the captured images are of sufficient quality for processing and analysis, the mobile app can include functionality for detecting the image quality, and alert the user to images that do not meet a quality threshold and thereby necessitate a retake. FIG. 5A illustrates an image 500 of sufficient quality, in which the lighting is satisfactory and the patient and color calibration target are both clearly visible. FIG. 5B illustrates a deficient image 502, in which portions of the image are obstructed by glare. FIG. 5C illustrates a deficient image 504, in which the image is too bright. FIG. 5D illustrates a deficient image 506, in which the color calibration target is partially obstructed. FIG. 5E illustrates a deficient image 508, in which the image is partially obscured by shadows. FIG. 5F illustrates a deficient image 510, in which the image is too dark.

Alternatively, the app may automatically recognize and save images with sufficient quality, without manual input from the user. In many embodiments, rather than checking the image quality after recording, the app can check the live image feed from the camera in real time, and alert the user of any potential images prior to image collection. Optionally, the app can automatically determine and report the source of image quality issues, and offer suggestions to the user for how to adjust accordingly.

Figure 6:
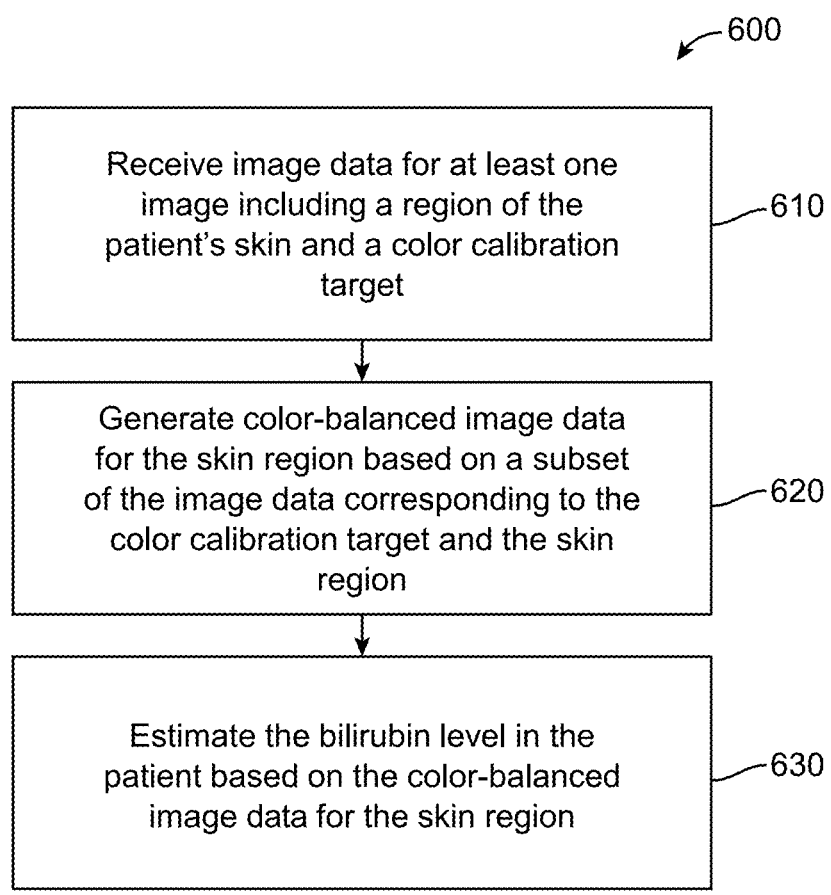
FIG. 6 illustrates a method for estimating the bilirubin level in a patient, in accordance with many embodiments.

FIG. 6 illustrates a method 600 for estimating the bilirubin level in a patient, in accordance with many embodiments. The method 600, as with all other methods described herein, can be practiced using any of the systems and devices disclosed herein, such as a mobile device or a separate computing system (e.g., a remote server) in communication with a mobile device. Certain steps of the method 600, as with all other methods described herein, can be optional, or may be combined with or substituted for suitable steps of other methods disclosed herein.

In act 610, image data is received for at least one image including a region of the patient's skin and a color calibration target. The image data can be collected using the camera of a mobile device, as previously described herein. Image data can include photographic data (e.g., a single image or a sequence of images), video data, or suitable combinations thereof. Photographic data and video data can be captured sequentially or simultaneously (e.g., images are taken during video recording). The image data can be obtained with and/or without using flash illumination. In some instances, flash illumination can be used to cancel out environmental lighting, such that the lighting in the resultant images is determined solely by contributions from the flash illumination. This can be advantageous to produce more consistent lighting or in situations where the environmental lighting is suboptimal (e.g., too dark, strongly colored, etc.).

In many embodiments, the image data is collected using a mobile app that controls the mobile device's flash unit, as well as the sequence and number of images taken. For example, the app can turn on the flash unit during the initial positioning of the mobile device, so that the user can assess the amount of glare in the image (e.g., via the video preview) and reposition the device as necessary to reduce or eliminate glare. During the recording process, the app can control the mobile device to first obtain image data with the flash unit on and then obtain image data with the flash unit off, thereby generating two image sets with and without flash illumination, respectively. For example, when the user initiates the image capture process (e.g., by pressing a record button), the app can be configured to record a video of the patient and calibration target, with the flash unit on for the first half and off for the second half. The app can also capture two photographs taken during the first and second halves of the video recording, respectively. The overall length of the video can be any suitable time, such as approximately 10 seconds. Alternatively or in combination, the app can be configured to capture a sequence of still images both with and without flash. The timing of the image capture process can further be configured to ensure that the image sensor (e.g., charge-coupled device (CCD) array) of the mobile device has stabilized before the next image is taken. For example, the app can include a specified amount of delay time (e.g., three to four seconds) before recording each image set.

As previously discussed, once the image capture sequence is complete, the mobile app can analyze the image data to determine whether it is of sufficient quality for subsequent use. For instance, the app can implement suitable image analysis techniques (e.g., computer vision) to assess image quality. An exemplary procedure involves extracting the color calibration target from the captured image data, checking the color consistency across each color region of the calibration target (e.g., determine whether the standard deviation of pixel values for each color region falls below a predetermined threshold), and recommending that the user retake any images that do not pass this test. In some instances, the app can be configured to capture multiple sets of image data per session, so as to maximize the likelihood that at least some of the image data will meet the quality standards. The approved images can then be processed on the mobile device or transmitted to a separate computing system for processing, as described in further detail below.

In act 620, color-balanced image data for the skin region is generated based on a subset of the image data corresponding to the color calibration target and the skin region. Color balancing can be performed in order to compensate for different lighting conditions, as the color content of the image data can vary considerably based on the environmental lighting (e.g., intensity, color, type (halogen, fluorescent, natural, etc.)). In many embodiments, the image data is initially normalized by dividing the three red, green, blue (RGB) color channels by the overall luminescence of the image. Furthermore, the observed pixel color values for one or more of the standardized color regions of the color calibration target can be used to determine the color balancing adjustments to be applied to the skin regions in the image data, as discussed below.

In act 630, the bilirubin level in the patient is estimated based on the color-balanced image data for the skin region. Since hyperbilirubinemia produces a yellow discoloration of the skin, the bilirubin level can be determined based on the amount of yellow in the color-balanced skin region image data. This determination can be performed using any suitable technique, such as by transforming the color-balanced image data into a plurality of different color spaces selected to facilitate quantifying the overall yellowness of the skin. Image features generated from the transformed image data can be input into a series of machine learning regressions designed to estimate the concentration of bilirubin in the patient's body. These approaches are discussed in further detail below.

Figure 7:
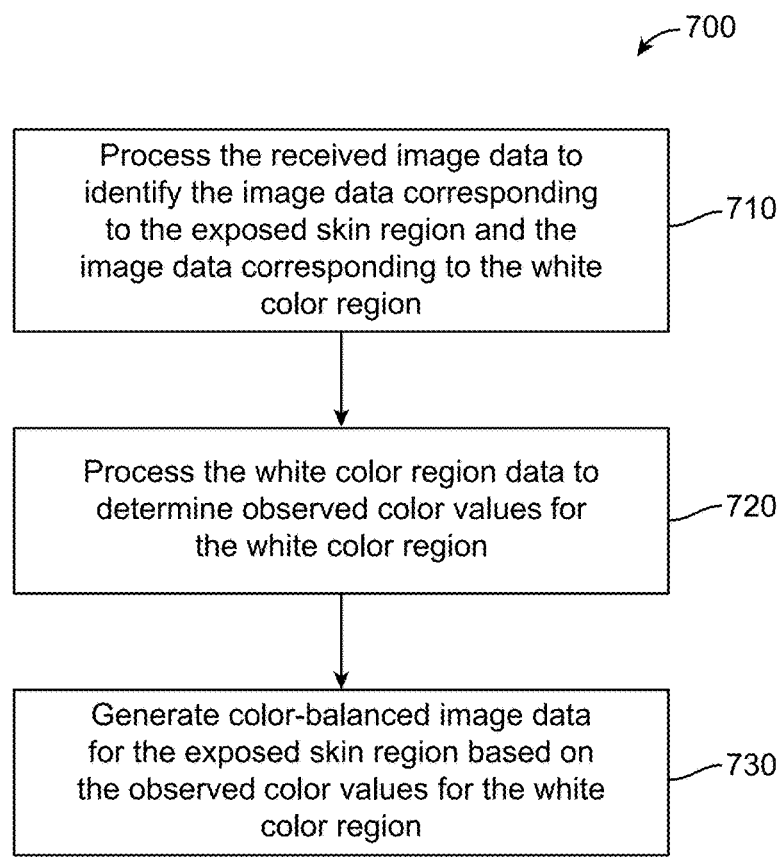
FIG. 7 illustrates a method for generating color-balanced image data for a patient's skin, in accordance with many embodiments.

FIG. 7 illustrates a method 700 for generating color-balanced image data, in accordance with many embodiments. The method 700 can be applied to photographic and/or video data obtained of a patient's skin region and color calibration target, as previously discussed. In act 710, the received image data is processed to identify the image data corresponding to the exposed skin region and the image data corresponding to the white color region. For example, the image data can be segmented to extract the pixel values of the color regions of the color calibration target and the skin regions of interest (e.g., sternum, forehead). With respect to the color calibration target, if the mobile app UI includes a positioning target for aligning the calibration target (e.g., positioning target 444 of FIG. 4C), then the approximate pixel coordinates of the color calibration target in the image data are already known, and the search space for the color regions can be constrained accordingly. The positioning of the color regions can be determined by identifying at least two color regions on the calibration target and using these as a basis for extrapolating the positions of the rest of the color regions.

Figure 8:
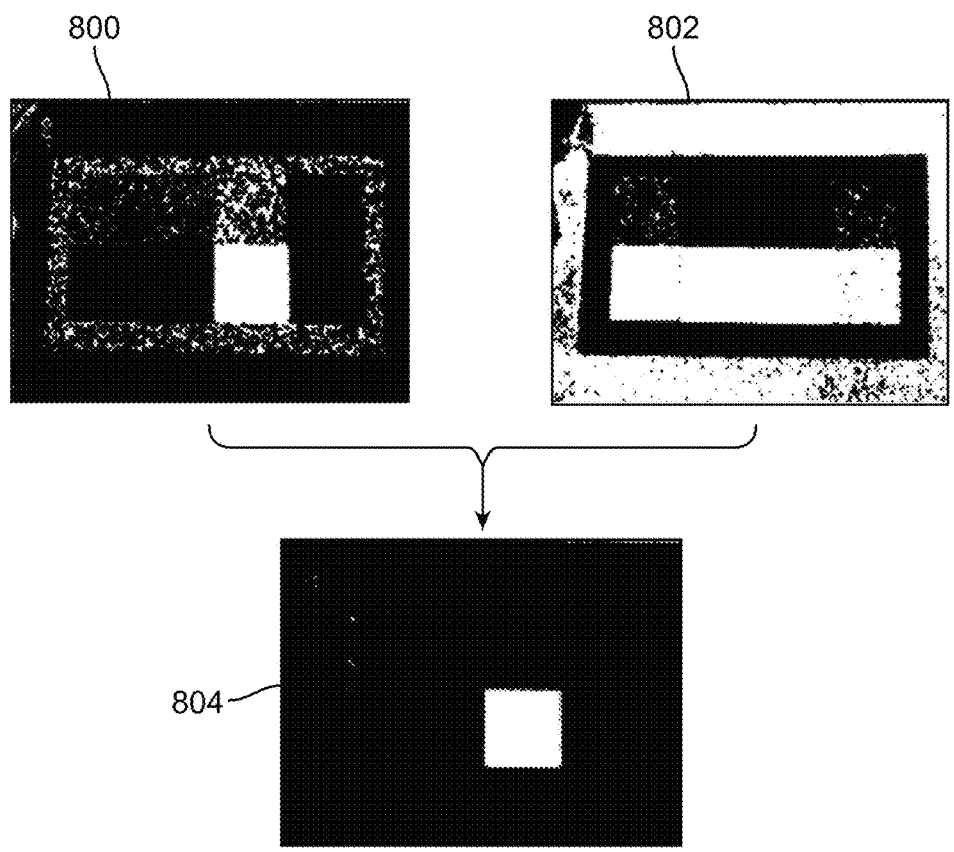
FIG. 8 illustrates identification of a standardized color region in an image, in accordance with many embodiments.

FIG. 8 illustrates identification of a standardized color region in an image, in accordance with many embodiments. The color region segmentation process can be implemented via a suitable algorithm configured to apply predetermined thresholds to the image. In many embodiments, since the cyan, magenta, and yellow color regions have distinct hues and relatively high saturation, the algorithm initially attempts to identify at least two of these regions. The algorithm can convert the image data to a hue, saturation, value (HSV) color space and apply empirically determined thresholds to the hue and saturation channels, thereby obtaining a thresholded hue image 800 and thresholded saturation image 802. An "AND" operation can be performed on the two thresholded images to separate the specified color region from the rest of the image, thereby producing a segmented image 804. Furthermore, since the approximate size of each color region is predetermined, this information can be used to differentiate the color region from the noise in the image data (e.g., using edge detection, morphological operations, etc.). For example, the algorithm can utilize an opening operation and Canny edge detection. The algorithm can then use contour detection to identify the boundary of the color region, with contour smoothing performed using suitable techniques such as the Douglas-Peuker algorithm. Since the overall arrangement of the color regions is known, once the positions of two color regions are determined, the overall orientation of the calibration target can be calculated and used to extrapolate the positions of the other regions, including the white color region.

In act 720, the white color region data is processed to determine observed color values for the white color region. In act 730, color-balanced image data for the exposed skin region is generated based on the observed color values for the white color region. The observed color values for the white color region can include RGB color values, which can be used to adjust the RGB values of the image data for the skin region. For example, for observed color values for the white region x=(R', G', B'), the adjusted color values for the skin region (R, G, B) can be obtained by $$\begin{bmatrix} R \\ G \\ B \end{bmatrix} = \begin{bmatrix} 255/R'_w & 0 & 0 \\ 0 & 255/G'_w & 0 \\ 0 & 0 & 255/B'_w \end{bmatrix} \begin{bmatrix} R' \\ G' \\ B' \end{bmatrix}$$

where $K_w = (R_w', G_w', B_w')$ is the raw observed color values of the white region on the color calibration target. The observed color values for the white color region can then be used to perform white balancing of the image data.

Once color balancing has been performed, the image data can be processed to estimate the mean red, green, and blue values, and the gradients of colors in the skin region. Various color transformations can be employed to approximate properties in the skin such as hue, gamma, and saturation. The extracted properties can then be used as features in a stacked regression and classification algorithm, which results in a final estimate of the bilirubin level.

Figure 9A:
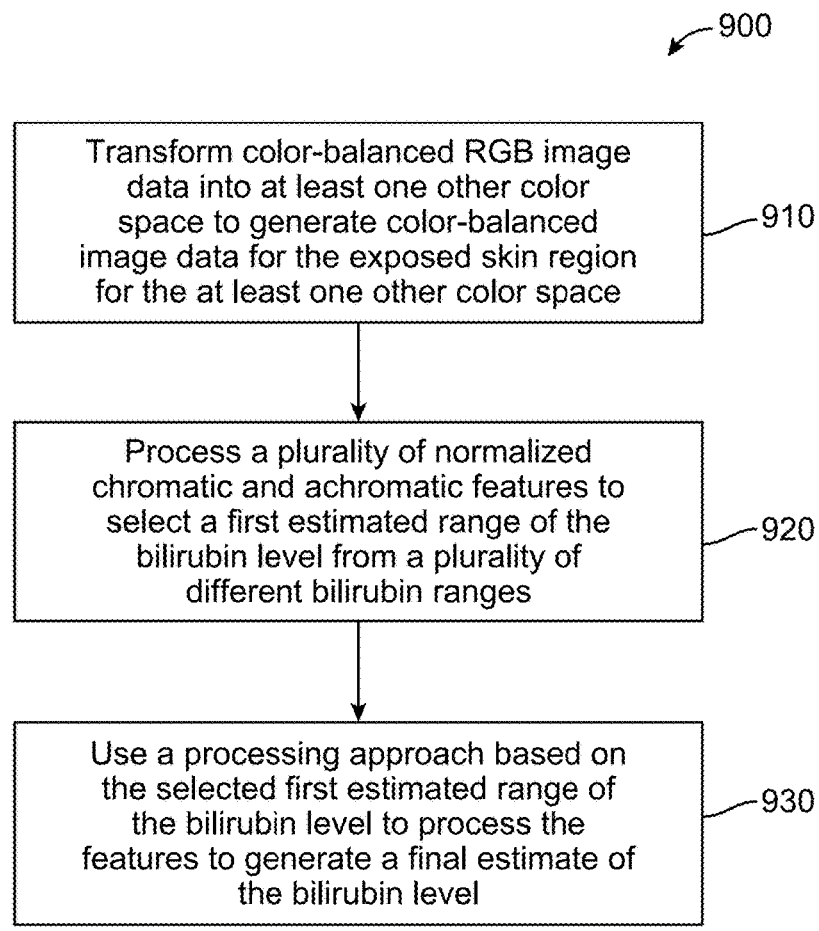
FIG. 9A illustrates a method for estimating the bilirubin level in a patient, in accordance with many embodiments.

FIG. 9A illustrates a method 900 for estimating the bilirubin level in a patient, in accordance with many embodiments. The method 900 can be practiced using color-balanced RGB image data obtained as previously described herein. In act 910, the color-balanced RGB image data is transformed into at least one other color space to generate color-balanced image data for the exposed skin region for the at least one other color space. As discussed above, the yellowness of the color-balanced skin region image data correlates to the bilirubin level in the patient's body. In many embodiments, the image sensor (e.g., CCD or CMOS sensor) of the mobile device interpolates reflected light into red, green, and blue wavelengths, which can prevent the image sensor from capturing the reflection of the yellow wavelength band clearly. Accordingly, the color-balanced RGB data can be transformed into a plurality of different color spaces, such as cyan, magenta, and yellow (CMY); cyan, magenta, yellow, and black (CMYK); YCbCr; or Lab color spaces. Any suitable number or combination of color spaces can be used. For example, in many embodiments, the RGB image data is transformed into CMYK, YCbCr, and Lab color spaces. Alternatively, the RGB image data can be transformed into CMY, YCbCr, and Lab color spaces.

Optionally, in addition to color transformations, a linear color gradient can be used to calculate the change in color across the portions of the image corresponding to the skin region. For example, the gradient can be calculated by running a 3×3 Sobel gradient filter across the color channel, and then averaging the outputs inside the portion. This can be performed in the red, blue, and green color planes, thus resulting in three additional features.

In act 920, a plurality of normalized chromatic and achromatic features are processed to select a first estimated range of the bilirubin level from a plurality of different bilirubin ranges. The features can be chromatic and/or achromatic values or properties (e.g., luminescence, hue, gamma, saturation) for the skin region, with each feature corresponding to a color space value of the color spaces used. In some instances, the features can include calculations of one or more color gradients across the skin the region. Any suitable number and combination of features can be used. For example, three features can be extracted from each of four color spaces (e.g., RGB, CMY, YCbCr, Lab; or RGB, CMYK, YCbCr, Lab) to obtain 12 chromatic and achromatic features. Furthermore, features can be separately extracted from image data obtained with flash illumination and without flash illumination, respectively, resulting in a total of 24 chromatic and achromatic features. As another example, 12 color planes can be obtained from each image of the skin region (three planes from each of four color spaces). The mean and median can be used in calculating one feature value from each region, thus resulting in 24 features per skin region. These 24 features can be calculated for each flash and non-flash image. Together with the color gradient features, this results in a total of 24+24+6=54 features.

The features can be normalized based on the overall luminescence of the image, as previously described herein with respect to act 620 of the method 600. Optionally, the features can be preprocessed to have unit variance and zero mean. The extracted features can be used as inputs to machine learning regressions used for estimating the bilirubin level. The regressions can utilize some or all of the extracted features, with the optimal subset of features to be used selected based on machine learning techniques. The machine learning regressions described herein can be trained on suitable data sets, such as clinical patient data, and can incorporate any suitable number and combination of parametric and non-parametric regression models. Exemplary regressions suitable for use with the methods described herein are provided below. In many embodiments, the initially calculated features and the output of the selected regressors are used to classify the estimated bilirubin level into one of a plurality of different bilirubin ranges, such as low, medium, and high ranges.

In act 930, the features are processed using a processing approach based on the selected first estimated range of the bilirubin level to generate a final estimate of the bilirubin level. Similar to the act 920, the normalized chromatic and achromatic features can be used to inform one or more machine learning regressions. The inputs to the regressions can differ based on whether the first estimated range of the bilirubin level is low, medium, or high, as provided in greater detail below. For example, the classification of the first estimated range can be used as input to the machine learning regressions. The results of the initial regression performed in act 920 can also be used as input. This "two-tiered" approach to bilirubin estimation can be used to generate more accurate estimation results compared to direct estimation.

Figure 9B:
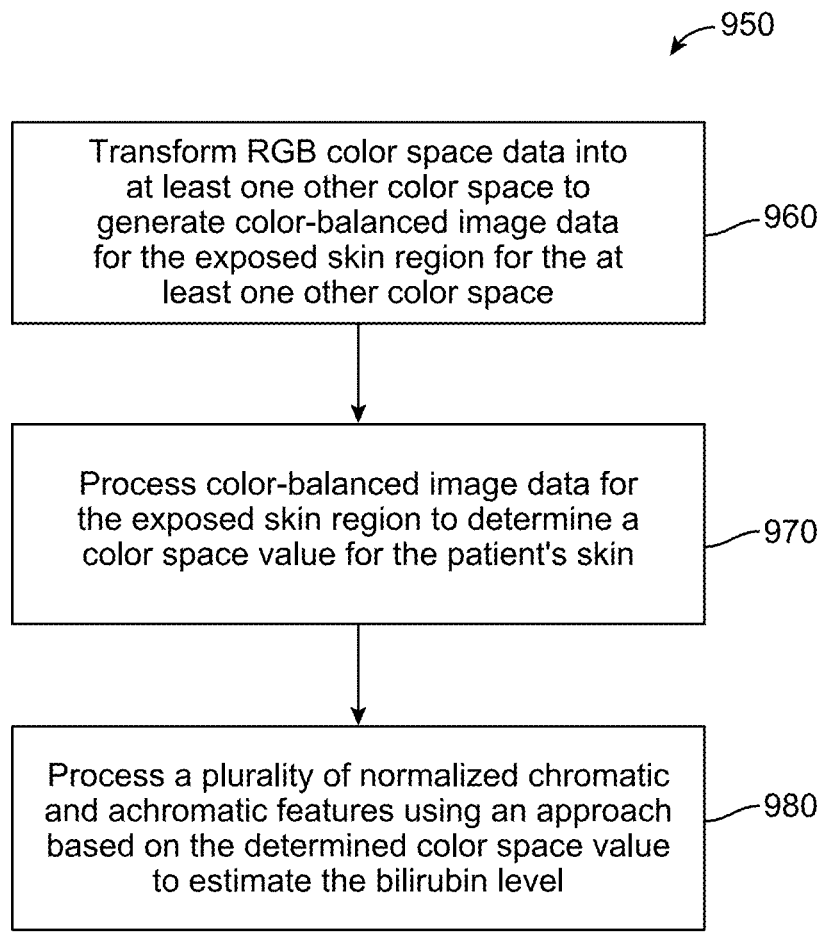
FIG. 9B illustrates another example of a method for estimating the bilirubin level in a patient, in accordance with many embodiments.

FIG. 9B illustrate a method 950 for estimating the bilirubin level in a patient, in accordance with many embodiments. The method 950 can be practiced in combination with the method 900 in order to obtain a more accurate estimate of the bilirubin level. Similar to the method 900, the method 950 can be practiced using color-balanced RGB image data obtained as previously described herein. In act 960, the color-balanced RGB image data is transformed into at least one other color space to generate color-balanced image data for the exposed skin region for the at least one other color space, as discussed above with respect to act 910 of the method 900.

In act 970, the color-balanced image data for the exposed skin region is processed to determine a color space value for the patient's skin. The color space value for the patient's skin can be used to classify the patient's skin color into one of a plurality of different skin color types, such as light-skinned, medium-skinned, and dark-skinned. The skin color type can be related to the race and/or ethnicity of the patient. The skin color type can be determined based on the color values of the skin region and/or color calibration target obtained from the color-balanced RGB image data. For example, the skin region can be compared to one or more standardized color regions of the color calibration target (e.g., the first and second skin tone color regions) to determine a skin color type.

In act 980, a plurality of normalized chromatic and achromatic features are processed using an approach based on the determined skin color to estimate the bilirubin level. The normalized chromatic and achromatic features can be extracted from the color-balanced image data for one or more different color spaces, as previously described above with respect to the method 900. The features, along with the determined skin color, can be used as inputs to suitable machine learning regressions, similar to the act 930 of the method 900.

As discussed above and herein, a custom machine learning regression can be used to estimate the bilirubin level. The regression algorithm can employ several different types of regressions that are parametric, non-parametric, and mixed. The regression algorithm can include a first step in which all of the features are used in each regression aimed at estimating the total bilirubin level, and a second step in which the outputs of each regression are averaged, thus resulting in a single value for the bilirubin level. In many embodiments, the output of the regression and the age of the patient are used to categorize the bilirubin value as low risk, intermediate low risk, intermediate high risk or high risk using the Bhutani nomogram described herein.

Figure 10:
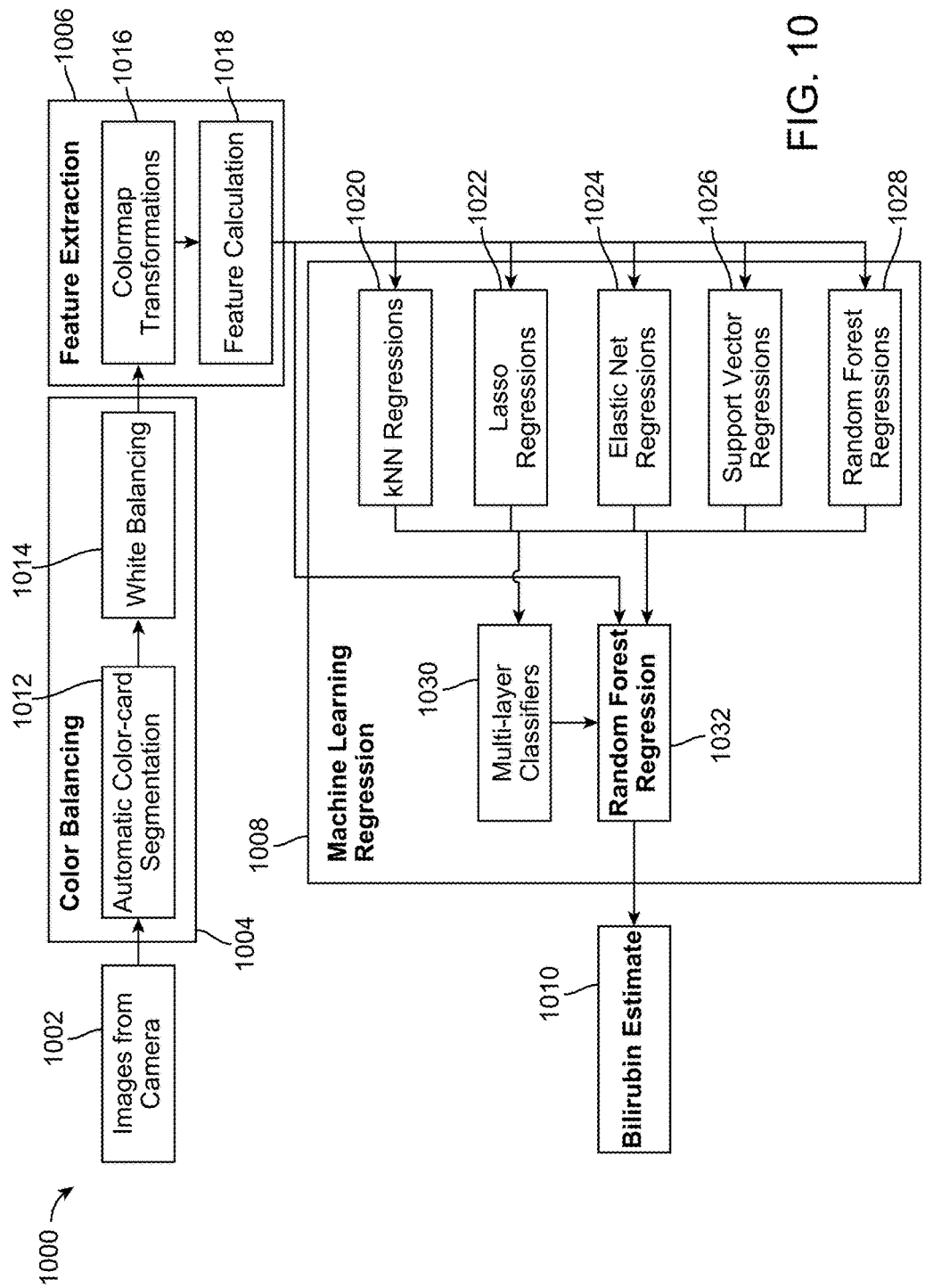
FIG. 10 illustrates a method for estimating the bilirubin level in a patient, in accordance with many embodiments.

FIG. 10 illustrates a method 1000 for estimating the bilirubin level in a patient, in accordance with many embodiments. The method 1000 includes obtaining images from a camera 1002, color balancing the image data 1004, performing feature extraction from the color-balanced image data 1006, performing machine learning regression based on the features 1008, and generating a bilirubin estimate 1010.

Image data can be obtained from the camera of a mobile device under the control of a suitable mobile app (act 1002). Some of the image data can be obtained with flash illumination and some of the image data can be obtained without flash illumination. Once the app has verified that the images are of sufficient quality for processing and analysis, the image data can be color balanced (act 1004). The color balancing can involve identification of the image data subsets corresponding to the color calibration target, and automatic segmentation of the standardized color regions of the target (act 1012) using the thresholding methods previously described herein. The segmented white color region can be used to white balance the image data (act 1014), thereby generating color-balanced image data. The color-balanced image data can be RGB image data. One or more features can be extracted from the color-balanced image data (act 1006). The feature extraction process can involve transforming the image data from an RGB color space to a plurality of different color spaces (act 1016), as previously described herein. The transformed image data can then be used to calculate a plurality of normalized chromatic and achromatic features (act 1018).

Some or all of the extracted features can be used as inputs to machine learning regressions (act 1008). Any suitable number and/or combination of regressions can be used. For example, an initial set of machine learning regressions can include five different sets of regressions (acts 1020, 1022, 1024, 1026, and 1028). For example, the first regression can include one or more encapsulated k-Nearest Neighbor (kNN) regressions (e.g., with k=7) (act 1020). This regression can utilize a database of known features and bilirubin values. When an unknown test vector is analyzed, the k-nearest neighbors can be found around the test vector in the database of features. A number of different distance metrics can be used to calculate the nearest neighbors, including the L1 and L2 norms. In many embodiments, a custom distance metric that cubes the differences between the samples and sums them together can is also used. Feature points from the neighbors can then be used in a linear regression (e.g., a linear support vector regression). A new regression can be built each time that a new test point is analyzed. The parameters for finding the nearest neighbors can be normalized values of luminosity (e.g., from the YCbCr color space transform) and the "green" or "red" channel (e.g., from the RGB color space). This can be used to guarantee that the nearest neighbor calculation only occurs in two dimensions, thus ensuring the number of points in the nearest neighbor is tractable (e.g., approximately four to six points).

The second regression can include one or more lasso regressions and/or one or more least angle regressions (LARS) (act 1022). LARS can be helpful for deciding which features out of the total set of extracted features are the most useful, using a variant of forward feature selection. For example, the best predictor(s) from the feature set can be chosen by developing a single-feature, linear regression from each feature. The most correlated output can be chosen as the "first" feature. This prediction can be subtracted from the output to obtain the residuals. The algorithm can diverge from other forward feature selection algorithms in that it attempts to find another feature with roughly the same correlation to the residuals as the first feature to the output. It can then find the "equiangular" direction between the two estimates, and can find a third feature that maximizes correlation to the new residuals along the equiangular direction. A new angle can then be found from the previous features and a new feature added to the set. Features can be added in this way until the desired accuracy is met.

The third regression can include one or more elastic net regressions, also known as elastic net algorithms (act 1024). The elastic net regression is a combination of Lasso regression (highly related to LARS for forward feature selection) and ridge regression (which uses an L2 regularization). Instead of just using forward feature selection, however, the algorithm can also employ the L1 and L2 norms in its objective function. This makes it related to LARS and Lasso, but with certain "backoff" regularization so that it can become more stable. The parameters can be cross-validated using a stepwise exhaustive search.

The fourth regression can include one or more support vector (SV) regressions (act 1026). Two SV regressions can be employed in order to capture the possible non-linear relationship between the image data and the bilirubin levels. SV regression can be used to find a linear regression function in a high dimensional feature space. Then, the input data can be mapped into the space using a potentially nonlinear function. The first SV regression can uses a linear kernel and the second SV regression can assign higher weight to higher-rated bilirubin values using a nonlinear radial or sigmoidal basis function.

The fifth regression can include one or more random forest regressions (act 1028). For example, the fifth regression can use a random forest regression with 75 or 500 trees. A random forest is a collection of estimators. It can use many "classifying" decision trees on various sub-samples of the dataset. The outputs of these trees can be averaged to improve the predictive accuracy and to control over-fitting. Each tree can be created using a random sub-sample (with replacement).

In many embodiments, other types of regressions can also be used in addition to or substituted for one or more of the regressions described herein. For example, one or more linear regressions can be also used. The method 1000 can be practiced using any suitable type of regression, including linear and non-linear regressions.

Following the initial regressions, one or more multi-layer classifiers can be used (act 1030). For example, the initially calculated features, along with the output of the initial set of regressors, can be used to classify a first estimated range of the bilirubin level into one of a plurality of different bilirubin ranges, as previously described herein. The classifiers can include a random forest classifier, a support vector machine, and a k-Nearest Neighbor (k=3). The results of all the classifiers, as well as the log-likelihood for each class, can be used as the features for a final stacked regression, which can be a final random forest regression (act 1032). The original extracted features and the results of the initial regressions can also be used as the features for this final stage regression. The final regressor can be trained using suitable machine learning algorithms, such as AdaBoost. The final regressor can be used as the final estimate of the bilirubin level 1010 (e.g., measured in milligrams per deciliter). In order to avoid overfitting, leave-one-out cross validation can be used at all levels of learning.

In alternative embodiments, the final regression output can be the mean of the different regressions performed. In such embodiments, acts 1030 and 1032 would be omitted and the outputs of the acts 1020, 1022, 1024, 1026, and 1028 would be averaged to obtain the final bilirubin estimate 1010.

Figure 11A:
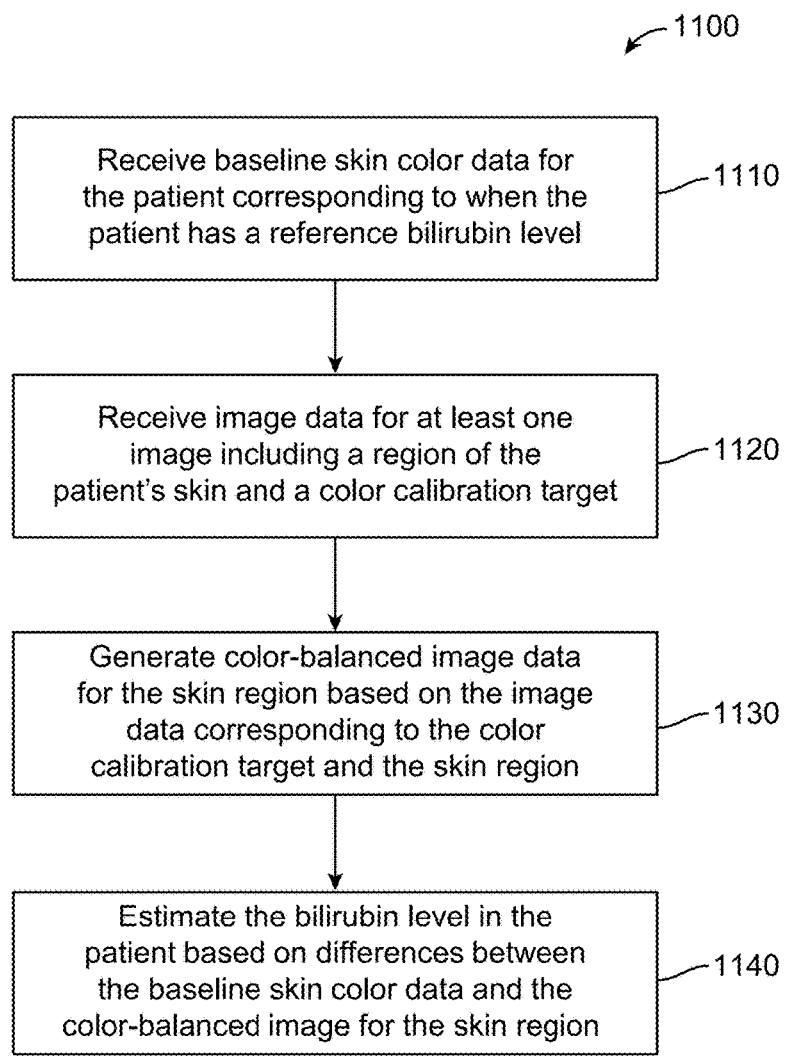
FIG. 11A illustrates a method for estimating the bilirubin level using baseline skin color data, in accordance with many embodiments.

FIG. 11A illustrates a method 1100 for estimating the bilirubin level in a patient using baseline skin color data, in accordance with many embodiments. The method 1100 is similar to the method 600, except that the current skin color data of the patient is compared to baseline skin color data in order to generate the bilirubin estimate. This approach can be used to compensate for factors that may confound the image analysis, such as differing skin tones due to the patient's race or ethnicity.

In act 1110, baseline skin color data for the patient is received, the baseline skin color data corresponding to when the patient has a reference bilirubin level. The reference bilirubin level can be a known bilirubin level (e.g., based on TSB or TcB testing). If the patient is an infant, the baseline skin color data can be collected within the first 24 hours of the infant's birth, when the bilirubin level is typically very low, such as approximately zero. Suitable methods for collecting and generating baseline skin color data are described below.

In act 1120, image data is received for at least one image including a region of the patient's skin and a color calibration target. In act 1130, color-balanced image data for the skin region is generated based on a subset of the image data corresponding to the color calibration target and the skin region. The image data collection and color-balancing processes can be similar to those previously described herein with respect to acts 610 and 620 of the method 600, respectively. The acts 1120 and 1130 can be performed at any time after the baseline skin color data is received and can be repeated over any suitable period of time (e.g., the first four to five days of the infant's life) so as to generate sequential image data sets used to determine whether the skin is becoming more yellow.

In act 1140, the bilirubin level in the patient is estimated based on differences between the baseline skin color data and the color-balanced image data for the skin region. In many embodiments, the baseline skin color data serves as a standard against which the current image data is compared. As previously described herein with respect to act 630 of the method 600, the estimation can be performed by transforming the color-balanced image data into a plurality of color spaces, extracting features from the transformed image data, and then using the features for machine learning regressions to generate a bilirubin estimate. At least some of the regressions described herein can also use some or all of the features extracted from the baseline skin color data.

Figure 11B:
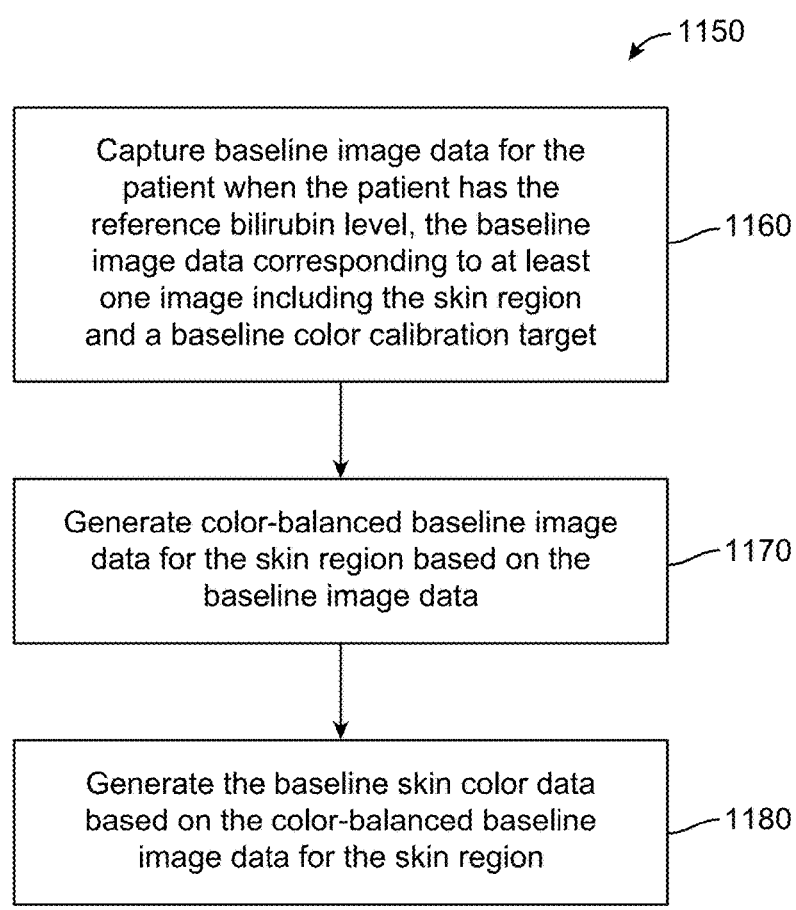
FIG. 11B illustrates a method for generating baseline skin color data, in accordance with many embodiments.

FIG. 11B illustrates a method 1150 for generating baseline skin color data, in accordance with many embodiments. In act 1160, baseline image data for the patient is captured when the patient has the reference bilirubin level, the baseline image data corresponding to at least one image including the skin region and a baseline color calibration target. The collection of the baseline image data can be similar to the collection procedures previously described herein with respect to act 610 of the method 600. The baseline color calibration target can be the same as the color calibration target used for collecting regular image data, or can be a different color calibration target. Similarly, the baseline image data can include the same skin regions as regular image data, or different skin regions. As described above, the reference bilirubin level can be any known bilirubin level, such as a bilirubin level determined by testing or taken within 24 hours of birth.

In act 1170, color-balanced baseline image data is generated for the skin region based on the baseline image data. The generation of the color-balanced baseline image data can be performed using any of the techniques previously described herein with respect to regular image data. In act 1180, the baseline skin color data is generated based on the color-balanced baseline image data for the skin region. This process can involve feature extraction from the color-balanced baseline image data and using the features for machine learning regressions, as discussed above.

Figure 12:
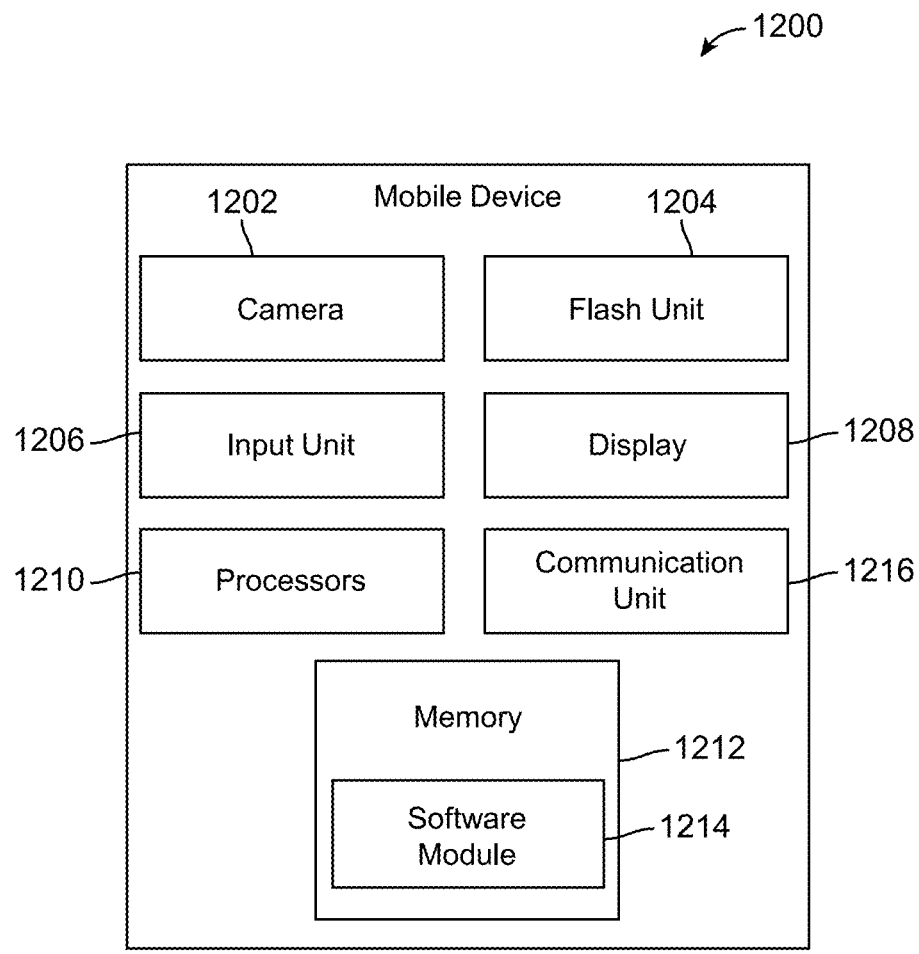
FIG. 12 illustrates a mobile device for estimating bilirubin level, in accordance with many embodiments.

FIG. 12 illustrates a mobile device 1200 for estimating bilirubin level in a patient, in accordance with many embodiments. The mobile device 1200 includes a camera 1202 suitable for capturing image data, and a flash unit 1204 suitable for providing flash illumination. The camera 1202 and flash unit 1204 can be built-in hardware of the mobile device 1200. Alternatively, the camera 1202 and flash unit 1204 can be provided separately from and coupled to the mobile device 1200 (e.g., via wired or wireless communication). In some instances, the mobile apps described herein can detect whether the camera 1202 is capable of capturing images with sufficiently high resolution for the subsequent image analysis, and can alert the user if this criterion is not met.

The mobile device 1200 also includes an input unit 1206 for receiving input from a user and a display 1208 for displaying content to the user. The input unit 1206 can include keyboards, mice, touchscreens, joysticks, and the like. The input unit 1206 can also be configured to accept voice commands or gestural commands. The display 1208 can include a monitor, screen, touchscreen, and the like. In some instances, the input unit 1206 and the display 1208 can be implemented across shared hardware (e.g., the same touchscreen is used to accept input and display output). As previously described, the display 1208 can display one or more suitable UIs to the user, such as UIs of a mobile app for estimating bilirubin levels.

The mobile device 1200 includes one or more processors 1210, a memory or other data storage device 1212 storing image data as well as one or more software modules 1214, and a communication unit 1216. The processors 1210 can be operably coupled to the camera 1202 and/or flash unit 1204 to control one or more functions (e.g., record function, zoom function, flash illumination function). The processor 1210 can also be operably coupled to the memory 1212 such that the processor 1210 can receive and execute instructions provided by the software module 1214. The software module 1214 can be implemented as part of the mobile apps described herein and can provide instructions for carrying out one or more acts of the previously discussed methods. For example, the software module 1214 can enable the mobile device 1200 to capture image data of a patient and calibration target. In some instances, the software module 1214 can perform some or all of the image processing and analysis tasks disclosed above (e.g., color balancing, feature extraction, machine learning regression). The software module 1214 can be adapted to a plurality of different types of mobile devices. Furthermore, the mobile device 1200 can be configured to receive and install software updates, such as updates improving one or more image capture, processing, and analysis algorithms, thereby enabling the mobile app to be easily and quickly upgraded as necessary.

The communication unit 1216 of the mobile device 1200 can be configured to receive and/or transmit data (e.g., image data, bilirubin estimates, software updates, etc.) between the mobile device 1200 and a separate device or system, such as a remote server or other computing system. The communication unit can use any suitable combination of wired or wireless communication methods, including Wi-Fi communication. In some instances, the communication between the mobile device 1200 and the separate device can be performed using short message service (SMS) text messaging. The communication unit 1216 can also be operably coupled to the processors 1210, such that data communication to and from the mobile device 1200 can be controlled based on instructions provided by the software module 1214.

Figure 13:
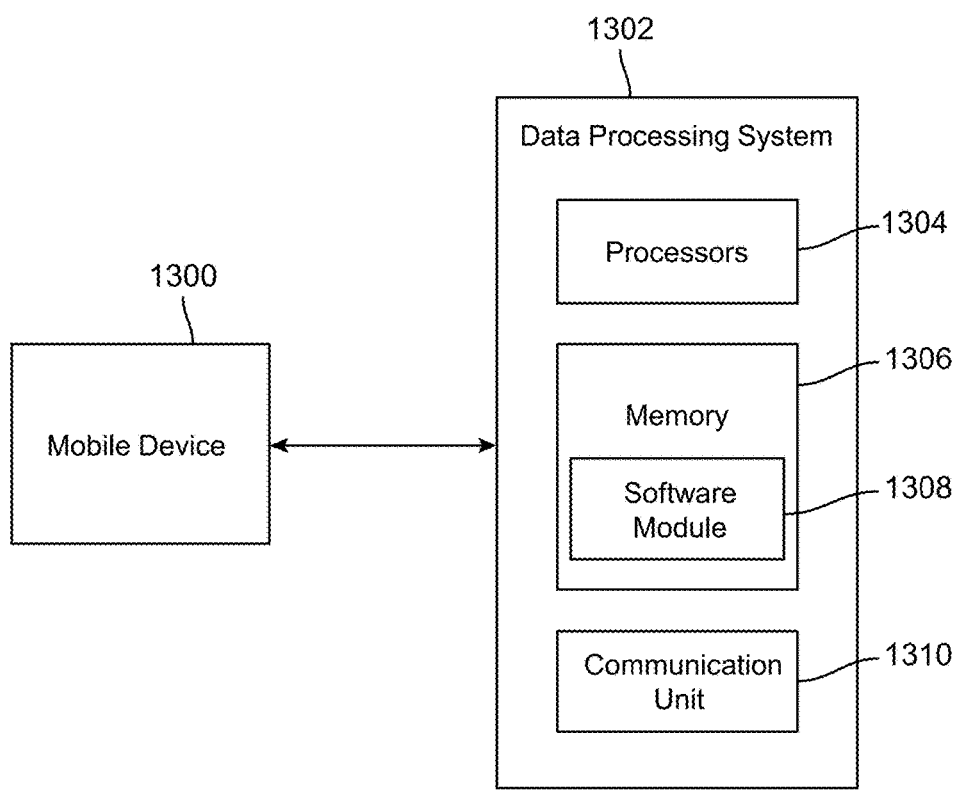
FIG. 13 illustrates a mobile device in a communication with a data processing system for estimating bilirubin level, in accordance with many embodiments.

FIG. 13 illustrates a mobile device 1300 in communication with a data processing system 1302 for estimating bilirubin levels, in accordance with many embodiments. The mobile device 1300 can include any of the components previously described herein with respect to the mobile device 1200 of FIG. 12. The components of the data processing system 1302 can be implemented across any suitable combination of physical and/or virtualized computing resources (e.g., virtual machines), including distributed computing resources ("in the cloud"). In many embodiments, the data processing system 1302 is a remote server configured to communicate with a plurality of user mobile devices including the mobile device 1300. The communication can utilize any suitable wired or wireless communication methods, as described above.

The data processing system 1302 includes one or more processors 1304, a memory or other data storage device 1306 storing one or more software modules 1308, and a communication unit 1310. The communication unit 1310 can be used to communicate data (e.g., image data, bilirubin estimates, software updates, etc.) between the system 1302 and the mobile device 1300 (e.g., via SMS text messaging). For example, the communication unit 1310 can receive image data provided by the mobile device 1300, such as image data that has not yet been color balanced. The data obtained from the mobile device 1300 can be stored in the memory 1306. The software module 1308 can provide instructions executable by the processors 1304 to process and analyze the image data (e.g., color balancing, feature extraction, machine learning regressions), such as by performing one or more acts of the methods described herein. The processors 1304 can output an estimate of the patient's bilirubin level, which can be stored in the memory 1306 and/or transmitted to the mobile device 1300. In some instances, depending on user preference, the results can also be transmitted to a third party, such as a medical professional who can review the results and provide the user with further instructions as necessary. Optionally, based on the results, the processors 1304 can also be configured to generate and display a recommended course of action to a user.

In an alternative embodiment, the mobile devices described herein can be configured to illuminate a patient's skin with different wavelengths of light (e.g., 460 nm, 540 nm) and capture images of the illuminated skin using a camera. The timing and sequence of illumination can be controlled by a mobile app. The mobile app can analyze the collected image data to measure the intensity of different wavelengths of light reflected from the skin regions. In many embodiments, the absorption of different wavelengths differs based on the color of the skin, including yellow discoloration. Some wavelengths can be affected by bilirubin levels, such that their intensities provide an indication of the amount of bilirubin in the patient's body. Accordingly, suitable machine learning regressions and/or models can be developed to enable wavelength absorption to be used as input for estimating bilirubin levels in a patient. Advantageously, this approach can be more robust to different environmental and situational conditions.

In many embodiments, the mobile device includes a front facing camera (e.g., a camera disposed on the same side of the mobile device as the screen) can be used to capture image data (e.g., photographs, videos) that is used to assess ambient lighting conditions. Such data provides alternative and/or additional ambient lighting information that can be used to normalize the color data of the patient's skin during estimation of the bilirubin level of the patient.

One of ordinary skill in the art would appreciate that any of the methods presented herein can be performed using a mobile device in combination with a data processing system ("server-connected" implementation) or using the mobile device alone ("stand-alone" implementation), as desired. A server-connected implementation may be advantageous for maintaining tighter control over how the system runs the estimation algorithm, as well as ensuring that the system is using the most up-to-date version of the algorithm. A stand-alone implementation may be advantageous in terms of allowing for the use of the estimation algorithm when Internet connectivity and/or cell coverage is incomplete or inadequate, e.g., in low resource settings.

Exemplary experimental bilirubin estimation results obtained in accordance with the methods herein are described in U.S. Provisional Application No. 62/041,492, which is incorporated herein by reference.

The various techniques described herein may be partially or fully implemented using code that is storable upon storage media and computer readable media, and executable by one or more processors of a computer system. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, solid state drives (SSD) or other solid state storage devices, or any other medium which can be used to store the desired information and which can be accessed by the a system device. Based on the disclosure and teachings provided herein, a person of ordinary skill in the art will appreciate other ways and/or methods to implement the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of estimating the level of bilirubin in a patient, the method comprising:
    receiving image data for at least one image including a region of the patient's skin and a color calibration target;
    generating color-balanced image data for the skin region based on a subset of the image data corresponding to the color calibration target and the skin region;
    estimating the bilirubin level in the patient based on the color-balanced image data for the skin region, wherein said estimating the bilirubin level comprises:
        processing a plurality of normalized chromatic and achromatic features to select a first estimated range of the bilirubin level from one of a plurality of different bilirubin ranges; and
        processing the features using an approach based on the selected first estimated range of the bilirubin level to generate a final estimate of the bilirubin level.

2. The method of claim 1, further comprising receiving baseline skin color data for the patient corresponding to when the patient has a reference bilirubin level, and wherein said estimating the bilirubin level is based on one or more differences between the baseline skin color data and the color-balanced image data for the skin region.

3. The method of claim 2, wherein the baseline skin color data for the patient is generated by:
    capturing baseline image data for the patient when the patient has the reference bilirubin level, the baseline image data corresponding to at least one image including the skin region and a baseline color calibration target;
    generating color-balanced baseline image data for the skin region based on a subset of the baseline image data corresponding to the baseline color calibration target and the skin region; and
    generating the baseline skin color data based on the color-balanced baseline image data for the skin region.

4. The method of claim 1, wherein the color calibration target comprises a plurality of standardized color regions including a white color region.

5. The method of claim 4, wherein the standardized color regions include a black region, a gray region, a light brown region, a cyan region, a magenta region, a yellow region, and a dark brown region.

6. The method of claim 4, wherein the color calibration target at least partially defines an opening configured to expose the skin region to permit capturing of image data for the skin region.

7. The method of claim 6, wherein the standardized color regions are disposed in a known arrangement surrounding the opening.

8. The method of claim 6, wherein said generating color-balanced image data for the skin region comprises:
    processing the received image data to identify a subset of the image data corresponding to the exposed skin region and a subset of the image data corresponding to the white color region;
    processing the white color region data to determine observed color values for the white color region; and
    generating color-balanced image data for the exposed skin region based on the observed color values for the white color region.

9. The method of claim 8, wherein the observed color values for the white color region comprise red, green, blue (RGB) color space values.

10. The method of claim 1, wherein the color-balanced image data for the skin region comprises RGB color space data, and the method further comprises transforming the RGB color space data into at least one other color space to generate color-balanced image data for the skin region for the at least one other color space.

11. The method of claim 10, wherein the at least one other color space includes: (a) a cyan, magenta, yellow, and black (CMYK) color space; (b) a YCbCr color space; or (c) a Lab color space.

12. The method of claim 10, wherein the at least one other color space include: (a) a cyan, magenta, yellow (CMY) color space; (b) a YCbCr color space; or (c) a Lab color space.

13. The method of claim 11, wherein the received image data includes an image obtained using flash illumination and an image obtained without using flash illumination.

14. The method of claim 13, wherein the plurality of different bilirubin ranges includes a loch range, a medium range, and a high range.

15. The method of claim 13, wherein the plurality of features comprises selected color values of the skin region for a plurality of different color spaces.

16. The method of claim 13, wherein the plurality of features comprise a calculation of a color gradient across the skin region.

17. The method of claim 13, wherein processing the features to select a first estimated range of the bilirubin level comprises performing a series of regressions including at least one of: (a) a linear regression, (b) an encapsulated k-Nearest Neighbor regression, (c) a lasso regression, (d) a LARS regression, (e) an elastic net regression, (f) a support vector regression using a linear kernel, (g) a support vector regression assigning higher weight to higher-rated bilirubin values, and (h) a random forest regression.

18. The method of claim 13, wherein processing the features to select a first estimated range of the bilirubin level comprises performing a series of regressions including: (a) a linear regression, an encapsulated k-Nearest Neighbor regression, (c) a lasso regression, (d) a LARS regression, (e) an elastic net regression, (f) a support vector regression using a linear kernel, (g) a support vector regression assigning higher weight to higher-rated bilirubin values, and (h) a random forest regression.

19. The method of claim 13, wherein said using a processing approach based on the selected first estimated range of the bilirubin level comprises performing a final random forest regression that uses the plurality of normalized chromatic and achromatic features and the selected first estimated range of the bilirubin level as the features for the final random forest regression.

20. The method of claim 1, wherein said estimating the bilirubin level comprises determining a color space value for the patient's skin and using a processing approach based on the determined patient's skin color space value to estimate the bilirubin level.

21. A mobile device configured to estimate the level of bilirubin in a patient, the mobile device comprising:
a camera operable to capture image data for a field of view;
a processor operatively coupled with the camera; and
a data storage device operatively coupled with the processor and storing instructions that, when executed by the processor, cause the processor to:
receive image data for an image captured by the camera, the image including a region of the patient's skin and a color calibration target;
generate color-balanced image data for the skin region based on a subset of the image data corresponding to the color calibration target and the skin region; and
estimate the bilirubin level in the patient based on the color-balanced image data for the skin region, wherein, to estimate the bilirubin level, the instructions further cause the processor to:
process a plurality of normalized chromatic and achromatic features to select a first estimated range of the bilirubin level from one of a plurality of different bilirubin ranges; and
process the features using an approach based on the selected first estimated range of the bilirubin level to generate a final estimate of the bilirubin level.

22. The mobile device of claim 21, wherein the color calibration target at least partially defines an opening configured to expose the skin region to permit capturing image data for the skin region and includes a plurality of standardized color regions including a white color region, and wherein the instructions cause the processor to:
process the received image data to identify a subset of the image data corresponding to the exposed skin region and a subset of the image data corresponding to the white color region;
process the white color region data to determine observed color values for the white color region;
generate color-balanced RGB image data for the exposed skin region based on the observed color values for the white color region; and
generate color-balanced image data for the exposed skin region for at least one other color space by transforming the color-balanced RGB image data into the at least one other color space.

23. The mobile device of claim 21, wherein the color calibration target at least partially defines an opening configured to expose the skin region to permit capturing image data for the skin region and includes a plurality of standardized color regions including a white color region, and wherein the instructions cause the processor to:
process the received image data to identify a subset of the image data corresponding to the exposed skin region and a subset of the image data corresponding to the white color region;
process the white color region data to determine observed color values for the white color region;
generate color-balanced RGB image data for the exposed skin region based on the observed color values for the white color region;
generate color-balanced image data for the exposed skin region for at least one other color space by transforming the color-balanced RGB image data into the at least one other color space;
process the color-balanced image data for the exposed skin region to determine a skin color for the patient; and
process the plurality of normalized chromatic and achromatic features using an approach based on the determined skin color to estimate the bilirubin level.

24. The mobile device of either one of claim 22 and claim 23, further comprising a flash unit operable to selectively illuminate the field of view, the received image data processed to estimate the bilirubin level including an image captured with the field of view being illuminated by the flash unit and an image captured with the field of view not being illuminated by the flash unit.

25. A method for estimating the level of bilirubin in a patient, the method comprising:
receiving, from a mobile device, image data for an image including a skin region of a patient and a color calibration target;
generating, via one or more processors, color-balanced image data for the skin region based on a subset of the image data corresponding to the color calibration target and the skin region;
estimating, via the one or more processors, the bilirubin level in the patient based on the color-balanced image data for the skin region, wherein said estimating the bilirubin level comprises:
processing a plurality of normalized chromatic and achromatic features to select a first estimated range of the bilirubin level from one of a plurality of different bilirubin ranges; and
processing the features using an approach based on the selected first estimated range of the bilirubin level to generate a final estimate of the bilirubin level; and transmitting the estimated bilirubin level to the mobile device.

26. The method of claim 25, wherein at least one of receiving the image data and transmitting the estimated bilirubin level are performed using short message service (SMS) text messaging.

\* \* \* \* \*